(12) United States Patent
Southard et al.

(10) Patent No.: US 10,769,739 B2
(45) Date of Patent: Sep. 8, 2020

(54) SYSTEMS AND METHODS FOR MANAGEMENT OF INFORMATION AMONG MEDICAL PROVIDERS AND FACILITIES

(75) Inventors: Jonathan Southard, Santa Barbara, CA (US); Scott Ross, Santa Barbara, CA (US); Timothy C Wright, Santa Barbara, CA (US); Dan Habecker, Santa Barbara, CA (US); Jennifer Neisse, Santa Barbara, CA (US); Elizabeth E Thomas, Ventura, CA (US); Andre Grujovski, Santa Barbara, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days.

(21) Appl. No.: 13/093,386

(22) Filed: Apr. 25, 2011

(65) Prior Publication Data
US 2012/0271648 A1    Oct. 25, 2012

(51) Int. Cl.
*G06Q 50/22*    (2018.01)
*G06Q 10/10*    (2012.01)
(Continued)

(52) U.S. Cl.
CPC .............. *G06Q 50/22* (2013.01); *G06Q 10/10* (2013.01); *G16H 10/20* (2018.01); *G16H 10/60* (2018.01); *G16H 40/20* (2018.01)

(58) Field of Classification Search
CPC ........ G06Q 50/22; G06Q 10/10; G16H 10/60; G16H 10/20; G16H 40/20
See application file for complete search history.

(56) References Cited

U.S. PATENT DOCUMENTS

| 3,821,995 A | 7/1974 | Aghnides |
| 4,107,689 A | 8/1978 | Jellinek |

(Continued)

FOREIGN PATENT DOCUMENTS

| AU | 1216200 A | 5/2000 |
| CA | 2289697 | 11/1998 |

(Continued)

OTHER PUBLICATIONS

Adams, Chris, "Mobile Robotics Research Group", Mobile Robotics Research Group, Edinburgh University, http://www.dai.ed.ac.uk/groups/mrg/MRG.html, Internet, Edinburgh, 2000, pp. 1-2.

(Continued)

*Primary Examiner* — Eliza A Lam

(57) ABSTRACT

Disclosed herein are various embodiments of the systems and methods for management of information among various medical providers and/or facilities. According to various embodiments, the systems and methods disclosed herein may facilitate the completion of location specific forms in a variety of formats by medical professionals. Certain embodiments may be employed by remotely located medical professional utilizing telemedicine technologies. Such systems may provide medical professionals utilizing telemedicine technologies with a consistent interface for gathering and inputting patient information, while continuing to allow for the use of a wide variety of forms by different medical providers and facilities. In addition to facilitating the use of location-specific forms, the systems and methods for management of information disclosed herein may also be used for the collection of patient care metrics.

11 Claims, 7 Drawing Sheets

(51) Int. Cl.
　　　*G16H 10/20*　　(2018.01)
　　　*G16H 20/40*　　(2018.01)
　　　*G16H 10/60*　　(2018.01)
　　　*G16H 40/20*　　(2018.01)

(56) References Cited

U.S. PATENT DOCUMENTS

| | | | |
|---|---|---|---|
| 4,213,182 A | 7/1980 | Eichelberger et al. | |
| 4,413,693 A | 11/1983 | Derby | |
| 4,471,354 A | 8/1984 | Smith | |
| 4,519,466 A | 5/1985 | Shiraishi | |
| 4,553,309 A | 11/1985 | Hess et al. | |
| 4,572,594 A | 2/1986 | Schwartz | |
| 4,625,274 A | 11/1986 | Schroeder | |
| 4,638,445 A | 1/1987 | Mattaboni | |
| 4,652,204 A | 3/1987 | Arnett | |
| 4,669,168 A | 6/1987 | Tamura et al. | |
| 4,679,152 A | 7/1987 | Perdue | |
| 4,697,278 A | 9/1987 | Fleischer | |
| 4,697,472 A | 10/1987 | Hiyane | |
| 4,709,265 A | 11/1987 | Silverman et al. | |
| 4,733,737 A | 3/1988 | Falamak | |
| 4,751,658 A | 6/1988 | Kadonoff et al. | |
| 4,766,581 A | 8/1988 | Korn et al. | |
| 4,777,416 A | 11/1988 | George et al. | |
| 4,797,557 A | 1/1989 | Ohman | |
| 4,803,625 A | 2/1989 | Fu et al. | |
| 4,847,764 A | 7/1989 | Halvorson | |
| 4,875,172 A | 10/1989 | Kanayama | |
| 4,878,501 A | 11/1989 | Shue | |
| 4,942,512 A | 7/1990 | Kohno | |
| 4,942,538 A | 7/1990 | Yuan et al. | |
| 4,953,159 A | 8/1990 | Hayden et al. | |
| 4,974,607 A | 12/1990 | Miwa | |
| 4,977,971 A | 12/1990 | Crane et al. | |
| 5,006,988 A | 4/1991 | Borenstein et al. | |
| 5,040,116 A | 8/1991 | Evans, Jr. et al. | |
| 5,051,906 A | 9/1991 | Evans, Jr. et al. | |
| 5,073,749 A | 12/1991 | Kanayama | |
| 5,084,828 A | 1/1992 | Kaufman | |
| 5,130,794 A | 7/1992 | Ritchey | |
| 5,148,591 A | 9/1992 | Pryor | |
| 5,153,833 A | 10/1992 | Gordon et al. | |
| 5,155,684 A | 10/1992 | Burke et al. | |
| 5,157,491 A | 10/1992 | Kassatly | |
| 5,182,641 A | 1/1993 | Diner et al. | |
| 5,186,270 A | 2/1993 | West | |
| 5,193,143 A | 3/1993 | Kaemmerer et al. | |
| 5,217,453 A | 6/1993 | Wilk | |
| 5,220,263 A | 6/1993 | Onishi et al. | |
| 5,224,157 A | 6/1993 | Yamada et al. | |
| 5,230,023 A | 7/1993 | Nakano | |
| 5,231,693 A | 7/1993 | Backes et al. | |
| 5,236,432 A | 8/1993 | Matsen, III et al. | |
| 5,262,944 A | 11/1993 | Weisner et al. | |
| 5,305,427 A | 4/1994 | Nagata | |
| 5,315,287 A | 5/1994 | Sol | |
| 5,319,611 A | 6/1994 | Korba | |
| 5,341,242 A | 8/1994 | Gilboa et al. | |
| 5,341,459 A | 8/1994 | Backes | |
| 5,341,854 A | 8/1994 | Zezulka et al. | |
| 5,347,306 A | 9/1994 | Nitta | |
| 5,347,457 A | 9/1994 | Tanaka et al. | |
| 5,350,033 A | 9/1994 | Kraft | |
| 5,366,896 A | 11/1994 | Margrey | |
| 5,374,879 A | 12/1994 | Pin | |
| 5,375,195 A | 12/1994 | Johnston | |
| 5,400,068 A | 3/1995 | Ishida et al. | |
| 5,413,693 A | 5/1995 | Redepenning | |
| 5,417,210 A | 5/1995 | Funda et al. | |
| 5,419,008 A | 5/1995 | West | |
| 5,436,542 A | 7/1995 | Petelin et al. | |
| 5,153,833 B1 | 8/1995 | Gordon et al. | |
| 5,441,042 A | 8/1995 | Putman | |
| 5,441,047 A | 8/1995 | David et al. | |
| 5,442,728 A | 8/1995 | Kaufman et al. | |
| 5,462,051 A | 10/1995 | Oka | |
| 5,486,853 A | 1/1996 | Baxter et al. | |
| 5,510,832 A | 4/1996 | Garcia | |
| 5,511,147 A | 4/1996 | Abdel-Malek | |
| 5,528,289 A | 6/1996 | Cortjens et al. | |
| 5,539,741 A | 7/1996 | Barraclough et al. | |
| 5,544,649 A | 8/1996 | David et al. | |
| 5,550,577 A | 8/1996 | Verbiest et al. | |
| 5,553,609 A | 9/1996 | Chen et al. | |
| 5,563,998 A * | 10/1996 | Yaksich et al. | 715/209 |
| 5,572,229 A | 11/1996 | Fisher | |
| 5,572,999 A | 11/1996 | Funda et al. | |
| 5,594,859 A | 1/1997 | Palmer et al. | |
| 5,600,573 A | 2/1997 | Hendricks et al. | |
| 5,617,539 A | 4/1997 | Ludwig et al. | |
| 5,619,341 A | 4/1997 | Auyeung et al. | |
| 5,623,679 A | 4/1997 | Rivette et al. | |
| 5,630,566 A | 5/1997 | Case | |
| 5,636,218 A | 6/1997 | Ishikawa et al. | |
| 5,652,849 A | 7/1997 | Conway et al. | |
| 5,657,246 A | 8/1997 | Hogan et al. | |
| 5,659,779 A | 8/1997 | Laird et al. | |
| 5,673,082 A | 9/1997 | Wells et al. | |
| 5,675,229 A | 10/1997 | Thorne | |
| 5,682,199 A | 10/1997 | Lankford | |
| 5,684,695 A | 11/1997 | Bauer | |
| 5,701,904 A | 12/1997 | Simmons et al. | |
| 5,734,805 A | 3/1998 | Isensee et al. | |
| 5,739,657 A | 4/1998 | Takayama et al. | |
| 5,748,629 A | 5/1998 | Caldara et al. | |
| 5,749,058 A | 5/1998 | Hashimoto | |
| 5,749,362 A | 5/1998 | Funda et al. | |
| 5,754,631 A | 5/1998 | Cave | |
| 5,758,079 A | 5/1998 | Ludwig et al. | |
| 5,762,458 A | 6/1998 | Wang et al. | |
| 5,764,731 A | 6/1998 | Yablon | |
| 5,767,897 A | 6/1998 | Howell | |
| 5,786,846 A | 7/1998 | Hiroaki | |
| 5,787,545 A | 8/1998 | Colens | |
| 5,793,365 A | 8/1998 | Tang et al. | |
| 5,801,755 A | 9/1998 | Echerer | |
| 5,802,494 A | 9/1998 | Kuno | |
| 5,836,872 A | 11/1998 | Kenet et al. | |
| 5,838,575 A | 11/1998 | Lion | |
| 5,844,599 A | 12/1998 | Hildin | |
| 5,857,534 A | 1/1999 | DeVault et al. | |
| 5,867,494 A | 2/1999 | Krishnaswamy et al. | |
| 5,867,653 A | 2/1999 | Aras et al. | |
| 5,871,451 A | 2/1999 | Unger et al. | |
| 5,872,922 A | 2/1999 | Hogan et al. | |
| 5,999,977 A | 2/1999 | Riddle | |
| 5,876,325 A | 3/1999 | Mizuno et al. | |
| 5,911,036 A | 6/1999 | Wright et al. | |
| 5,917,958 A | 6/1999 | Nunally et al. | |
| 5,927,423 A | 7/1999 | Wada et al. | |
| 5,949,758 A | 9/1999 | Kober et al. | |
| 5,954,692 A | 9/1999 | Smith et al. | |
| 5,959,423 A | 9/1999 | Nakanishi et al. | |
| 5,961,446 A | 10/1999 | Beller et al. | |
| 5,966,130 A | 10/1999 | Benman | |
| 5,973,724 A | 10/1999 | Riddle | |
| 5,974,446 A | 10/1999 | Sonnenreich et al. | |
| 5,983,263 A | 11/1999 | Rothrock et al. | |
| 5,995,119 A | 11/1999 | Cosatto et al. | |
| 5,995,884 A | 11/1999 | Allen et al. | |
| 6,006,946 A | 12/1999 | Williams et al. | |
| 6,031,845 A | 2/2000 | Walding | |
| 6,036,812 A | 3/2000 | Williams et al. | |
| 6,047,259 A * | 4/2000 | Campbell et al. | 705/3 |
| 6,091,219 A | 7/2000 | Maruo et al. | |
| 6,113,343 A | 9/2000 | Goldenberg et al. | |
| 6,133,944 A | 10/2000 | Braun | |
| 6,135,228 A | 10/2000 | Asada et al. | |
| 6,148,100 A | 11/2000 | Anderson et al. | |
| 6,160,582 A | 12/2000 | Hill | |
| 6,170,929 B1 | 1/2001 | Wilson et al. | |
| 6,175,779 B1 | 1/2001 | Barrett | |
| 6,189,034 B1 | 2/2001 | Riddle | |

(56) References Cited

U.S. PATENT DOCUMENTS

| | | |
|---|---|---|
| 6,201,984 B1 | 3/2001 | Funda et al. |
| 6,211,903 B1 | 4/2001 | Bullister |
| 6,219,587 B1 | 4/2001 | Ahlin et al. |
| 6,232,735 B1 | 5/2001 | Baba et al. |
| 6,233,504 B1 | 5/2001 | Das et al. |
| 6,233,735 B1 | 5/2001 | Ebihara |
| 6,250,928 B1 | 6/2001 | Poggio et al. |
| 6,256,556 B1 | 7/2001 | Zenke |
| 6,259,806 B1 | 7/2001 | Green |
| 6,259,956 B1 | 7/2001 | Myers et al. |
| 6,266,162 B1 | 7/2001 | Okamura et al. |
| 6,266,577 B1 | 7/2001 | Popp et al. |
| 6,289,263 B1 | 9/2001 | Mukherjee |
| 6,292,713 B1 | 9/2001 | Jouppi et al. |
| 6,292,714 B1 | 9/2001 | Okabayashi |
| 6,304,050 B1 | 10/2001 | Skaar et al. |
| 6,314,631 B1 | 11/2001 | Pryor |
| 6,317,652 B1 | 11/2001 | Osada |
| 6,317,953 B1 | 11/2001 | Pryor |
| 6,321,137 B1 | 11/2001 | De Smet |
| 6,324,184 B1 | 11/2001 | Hou et al. |
| 6,324,443 B1 | 11/2001 | Kurakake et al. |
| 6,325,756 B1 | 12/2001 | Webb et al. |
| 6,327,516 B1 | 12/2001 | Zenke |
| 6,330,486 B1 | 12/2001 | Padula |
| 6,330,493 B1 | 12/2001 | Takahashi et al. |
| 6,346,950 B1 | 2/2002 | Jouppi |
| 6,346,962 B1 | 2/2002 | Goodridge |
| 6,369,847 B1 | 4/2002 | James et al. |
| 6,373,855 B1 | 4/2002 | Downing et al. |
| 6,381,515 B1 | 4/2002 | Inoue et al. |
| 6,389,329 B1 | 5/2002 | Colens |
| 6,400,378 B1 | 6/2002 | Snook |
| 6,408,230 B2 | 6/2002 | Wada |
| 6,411,055 B1 | 6/2002 | Fujita et al. |
| 6,430,471 B1 | 8/2002 | Kintou et al. |
| 6,430,475 B2 | 8/2002 | Okamoto |
| 6,438,457 B1 | 8/2002 | Yokoo |
| 6,445,964 B1 | 9/2002 | White et al. |
| 6,449,762 B1 | 9/2002 | McElvain |
| 6,452,915 B1 | 9/2002 | Jorgensen |
| 6,457,043 B1 | 9/2002 | Kwak et al. |
| 6,459,955 B1 | 10/2002 | Bartsch et al. |
| 6,463,352 B1 | 10/2002 | Tadokoro et al. |
| 6,463,361 B1 | 10/2002 | Wang |
| 6,466,844 B1 | 10/2002 | Ikeda et al. |
| 6,468,265 B1 | 10/2002 | Evans et al. |
| 6,470,235 B2 | 10/2002 | Kasuga et al. |
| 6,474,434 B1 | 11/2002 | Bech |
| 6,480,762 B1 | 11/2002 | Uchikubo et al. |
| 6,491,701 B2 | 12/2002 | Tierney |
| 6,496,099 B2 | 12/2002 | Wang et al. |
| 6,496,755 B2 | 12/2002 | Wallach et al. |
| 6,501,740 B1 | 12/2002 | Sun et al. |
| 6,507,773 B2 | 1/2003 | Parker et al. |
| 6,522,906 B1 | 2/2003 | Salisbury et al. |
| 6,523,629 B1 | 2/2003 | Buttz et al. |
| 6,526,332 B2 | 2/2003 | Sakamoto et al. |
| 6,529,620 B2 | 3/2003 | Thompson |
| 6,529,765 B1 | 3/2003 | Franck |
| 6,529,802 B1 | 3/2003 | Kawakita et al. |
| 6,532,404 B2 | 3/2003 | Colens |
| 6,535,182 B2 | 3/2003 | Stanton |
| 6,535,793 B2 | 3/2003 | Allard |
| 6,540,039 B1 | 4/2003 | Yu |
| 6,543,899 B2 | 4/2003 | Covannon et al. |
| 6,549,215 B2 | 4/2003 | Jouppi |
| 6,563,533 B1 | 5/2003 | Colby |
| 6,567,038 B1 | 5/2003 | Granot et al. |
| 6,580,246 B2 | 6/2003 | Jacobs |
| 6,581,798 B2 | 6/2003 | Liff et al. |
| 6,584,376 B1 | 6/2003 | Van Kommer |
| 6,587,750 B2 | 7/2003 | Gerbi et al. |
| 6,590,604 B1 | 7/2003 | Tucker et al. |
| 6,594,269 B1 | 7/2003 | Polcyn |
| 6,594,552 B1 | 7/2003 | Nowlin et al. |
| 6,597,392 B1 | 7/2003 | Jenkins et al. |
| 6,602,469 B1 | 8/2003 | Maus et al. |
| 6,604,019 B2 | 8/2003 | Ahlin et al. |
| 6,604,021 B2 | 8/2003 | Imai et al. |
| 6,611,120 B2 | 8/2003 | Song et al. |
| 6,643,496 B1 | 11/2003 | Shimoyama et al. |
| 6,646,677 B2 | 11/2003 | Noro et al. |
| 6,650,748 B1 | 11/2003 | Edwards et al. |
| 6,666,374 B1 | 12/2003 | Green et al. |
| 6,667,592 B2 | 12/2003 | Jacobs et al. |
| 6,674,259 B1 | 1/2004 | Norman et al. |
| 6,684,129 B2 | 1/2004 | Salisbury et al. |
| 6,691,000 B2 | 2/2004 | Nagai et al. |
| 6,693,585 B1 | 2/2004 | MacLeod |
| 6,710,797 B1 | 3/2004 | McNelley et al. |
| 6,724,823 B2 | 4/2004 | Rovati et al. |
| 6,728,599 B2 | 4/2004 | Wang et al. |
| 6,763,282 B2 | 7/2004 | Glenn et al. |
| 6,764,373 B1 | 7/2004 | Osawa et al. |
| 6,769,771 B2 | 8/2004 | Trumbull |
| 6,781,606 B2 | 8/2004 | Jouppi et al. |
| 6,784,916 B2 | 8/2004 | Smith |
| 6,785,589 B2 | 8/2004 | Eggenberger et al. |
| 6,791,550 B2 | 9/2004 | Goldhor et al. |
| 6,798,753 B1 | 9/2004 | Doganata et al. |
| 6,799,065 B1 | 9/2004 | Niemeyer |
| 6,799,088 B2 | 9/2004 | Wang et al. |
| 6,804,580 B1 | 10/2004 | Stoddard et al. |
| 6,804,656 B1 | 10/2004 | Rosenfeld et al. |
| 6,810,411 B1 | 10/2004 | Coughlin et al. |
| 6,816,192 B1 | 11/2004 | Nishikawa |
| 6,816,754 B2 | 11/2004 | Mukai et al. |
| 6,836,703 B2 | 12/2004 | Wang et al. |
| 6,839,612 B2 | 1/2005 | Sanchez et al. |
| 6,840,904 B2 | 1/2005 | Goldberg |
| 6,845,297 B2 | 1/2005 | Allard |
| 6,852,107 B2 | 2/2005 | Wang et al. |
| 6,853,878 B2 | 2/2005 | Hirayama et al. |
| 6,853,880 B2 | 2/2005 | Sakagami et al. |
| 6,871,117 B2 | 3/2005 | Wang et al. |
| 6,879,879 B2 | 4/2005 | Jouppi et al. |
| 6,888,333 B2 | 5/2005 | Laby |
| 6,892,112 B2 | 5/2005 | Wang et al. |
| 6,893,267 B1 | 5/2005 | Yueh |
| 6,895,305 B2 | 5/2005 | Lathan et al. |
| 6,898,484 B2 | 5/2005 | Lemelson et al. |
| 6,914,622 B1 | 7/2005 | Smith et al. |
| 6,925,357 B2 | 8/2005 | Wang et al. |
| 6,951,535 B2 | 10/2005 | Ghodoussi et al. |
| 6,952,470 B1 | 10/2005 | Tioe |
| 6,957,712 B2 | 10/2005 | Song et al. |
| 6,958,706 B2 | 10/2005 | Chaco et al. |
| 6,965,394 B2 | 11/2005 | Gutta et al. |
| 6,990,112 B1 | 1/2006 | Brent et al. |
| 6,995,664 B1 | 2/2006 | Darling et al. |
| 7,007,235 B1 | 2/2006 | Hussein et al. |
| 7,011,538 B2 | 3/2006 | Chang |
| 7,015,934 B2 | 3/2006 | Toyama et al. |
| RE39,080 E | 4/2006 | Johnston |
| 7,030,757 B2 | 4/2006 | Matsuhira et al. |
| 7,053,578 B2 | 5/2006 | Diehl et al. |
| 7,055,210 B2 | 6/2006 | Keppler et al. |
| 7,058,689 B2 | 6/2006 | Parker et al. |
| 7,092,001 B2 | 8/2006 | Schulz |
| 7,096,090 B1 | 8/2006 | Zweig |
| 7,115,102 B2 | 10/2006 | Abbruscato |
| 7,117,067 B2 | 10/2006 | McLurkin et al. |
| 7,123,285 B2 | 10/2006 | Smith et al. |
| 7,123,974 B1 | 10/2006 | Hamilton |
| 7,123,991 B2 | 10/2006 | Graf et al. |
| 7,127,325 B2 | 10/2006 | Nagata et al. |
| 7,129,970 B2 | 10/2006 | James et al. |
| 7,133,062 B2 | 11/2006 | Castles et al. |
| 7,142,945 B2 | 11/2006 | Wang et al. |
| 7,142,947 B2 | 11/2006 | Wang et al. |
| 7,151,982 B2 | 12/2006 | Liff |
| 7,154,526 B2 | 12/2006 | Foote et al. |
| 7,155,306 B2 | 12/2006 | Haitin et al. |

(56) References Cited

U.S. PATENT DOCUMENTS

| | | |
|---|---|---|
| 7,156,809 B2 | 1/2007 | Quy |
| 7,158,859 B2 | 1/2007 | Wang et al. |
| 7,158,860 B2 | 1/2007 | Wang et al. |
| 7,158,861 B2 | 1/2007 | Wang et al. |
| 7,161,322 B2 | 1/2007 | Wang et al. |
| 7,162,338 B2 | 1/2007 | Goncalves et al. |
| 7,164,969 B2 | 1/2007 | Wang et al. |
| 7,164,970 B2 | 1/2007 | Wang et al. |
| 7,167,448 B2 | 1/2007 | Wookey et al. |
| 7,171,286 B2 | 1/2007 | Wang et al. |
| 7,174,238 B1 | 2/2007 | Zweig |
| 7,181,455 B2 | 2/2007 | Wookey et al. |
| 7,184,559 B2 | 2/2007 | Jouppi |
| 7,188,000 B2 | 3/2007 | Chiappetta et al. |
| 7,199,790 B2 | 4/2007 | Rosenberg et al. |
| 7,202,851 B2 | 4/2007 | Cunningham et al. |
| 7,206,627 B2 | 4/2007 | Abovitz et al. |
| 7,215,786 B2 | 5/2007 | Nakadai et al. |
| 7,219,364 B2 | 5/2007 | Bolle et al. |
| 7,222,000 B2 | 5/2007 | Wang et al. |
| 7,227,334 B2 | 6/2007 | Yang et al. |
| 7,256,708 B2 | 8/2007 | Rosenfeld |
| 7,262,573 B2 | 8/2007 | Wang et al. |
| 7,283,153 B2 | 10/2007 | Provost et al. |
| 7,289,883 B2 | 10/2007 | Wang et al. |
| 7,292,257 B2 | 11/2007 | Kang et al. |
| 7,292,912 B2 | 11/2007 | Wang et al. |
| 7,305,114 B2 | 12/2007 | Wolff et al. |
| 7,317,685 B1 | 1/2008 | Flott et al. |
| 7,321,807 B2 | 1/2008 | Laski |
| 7,332,890 B2 | 2/2008 | Cohen et al. |
| 7,333,642 B2 | 2/2008 | Green |
| 7,346,429 B2 | 3/2008 | Goldenberg et al. |
| 7,352,153 B2 | 4/2008 | Yan |
| 7,363,121 B1 | 4/2008 | Chen et al. |
| 7,382,399 B1 | 6/2008 | McCall |
| 7,386,730 B2 | 6/2008 | Uchikubo |
| 7,391,432 B2 | 6/2008 | Terada |
| 7,400,578 B2 | 7/2008 | Guthrie et al. |
| 7,404,140 B2 * | 7/2008 | O'Rourke ............... 715/222 |
| 7,421,470 B2 | 9/2008 | Ludwig et al. |
| 7,430,209 B2 | 9/2008 | Porter |
| 7,432,949 B2 | 10/2008 | Remy et al. |
| 7,433,921 B2 | 10/2008 | Ludwig et al. |
| 7,441,953 B2 | 10/2008 | Banks |
| 7,467,211 B1 | 12/2008 | Herman et al. |
| 7,483,867 B2 | 1/2009 | Ansari et al. |
| 7,492,731 B2 | 2/2009 | Hagendorf |
| 7,510,428 B2 | 3/2009 | Obata et al. |
| 7,523,069 B1 | 4/2009 | Friedl et al. |
| 7,525,281 B2 | 4/2009 | Koyanagi et al. |
| 7,535,486 B2 | 5/2009 | Motomura et al. |
| 7,557,758 B2 | 7/2009 | Rofougaran |
| 7,587,260 B2 | 9/2009 | Bruemmer et al. |
| 7,587,512 B2 | 9/2009 | Ta et al. |
| 7,590,060 B2 | 9/2009 | Miceli |
| 7,593,030 B2 | 9/2009 | Way et al. |
| 7,599,290 B2 | 10/2009 | Dos Remedios et al. |
| 7,624,166 B2 | 11/2009 | Foote et al. |
| 7,630,314 B2 | 12/2009 | Dos Remedios et al. |
| 7,631,833 B1 | 12/2009 | Ghaleb et al. |
| 7,643,051 B2 | 1/2010 | Sandberg et al. |
| 7,647,320 B2 | 1/2010 | Mok et al. |
| 7,657,560 B1 | 2/2010 | DiRienzo |
| 7,680,038 B1 | 3/2010 | Gourlay |
| 7,693,757 B2 | 4/2010 | Zimmerman |
| 7,698,432 B2 | 4/2010 | Short et al. |
| 7,703,113 B2 | 4/2010 | Dawson |
| 7,719,229 B2 | 5/2010 | Kaneko et al. |
| 7,737,993 B2 | 6/2010 | Kaasila et al. |
| 7,739,383 B1 | 6/2010 | Short et al. |
| 7,756,614 B2 | 7/2010 | Jouppi |
| 7,761,185 B2 | 7/2010 | Wang et al. |
| 7,769,492 B2 | 8/2010 | Wang et al. |
| 7,769,705 B1 | 8/2010 | Luechtefeld |
| 7,774,158 B2 | 8/2010 | Domingues Goncalves et al. |
| 7,813,836 B2 | 10/2010 | Wang et al. |
| 7,831,575 B2 | 11/2010 | Trossell et al. |
| 7,835,775 B2 | 11/2010 | Sawayama et al. |
| 7,860,680 B2 | 12/2010 | Arms et al. |
| 7,861,366 B2 | 1/2011 | Hahm et al. |
| 7,885,822 B2 | 2/2011 | Akers et al. |
| 7,890,382 B2 | 2/2011 | Robb et al. |
| 7,912,583 B2 | 3/2011 | Gutmann et al. |
| RE42,288 E | 4/2011 | Degioanni |
| 7,924,323 B2 | 4/2011 | Walker et al. |
| 7,949,616 B2 | 5/2011 | Levy et al. |
| 7,956,894 B2 | 6/2011 | Akers et al. |
| 7,957,837 B2 | 6/2011 | Ziegler et al. |
| 7,982,763 B2 | 7/2011 | King |
| 7,982,769 B2 | 7/2011 | Jenkins et al. |
| 7,987,069 B2 | 7/2011 | Rodgers et al. |
| 8,077,963 B2 | 12/2011 | Wang et al. |
| 8,116,910 B2 | 2/2012 | Walters et al. |
| 8,126,960 B2 | 2/2012 | Obradovich et al. |
| 8,170,241 B2 | 5/2012 | Roe et al. |
| 8,179,418 B2 | 5/2012 | Wright et al. |
| 8,180,486 B2 | 5/2012 | Saito et al. |
| 8,209,051 B2 | 6/2012 | Yulun et al. |
| 8,212,533 B2 | 7/2012 | Ota |
| 8,265,793 B2 | 9/2012 | Cross et al. |
| 8,287,522 B2 | 10/2012 | Moses et al. |
| 8,292,807 B2 | 10/2012 | Perkins et al. |
| 8,320,534 B2 | 11/2012 | Kim et al. |
| 8,340,654 B2 | 12/2012 | Bratton et al. |
| 8,340,819 B2 | 12/2012 | Mangaser et al. |
| 8,348,675 B2 | 1/2013 | Dohrmann |
| 8,374,171 B2 | 2/2013 | Cho et al. |
| 8,400,491 B1 | 3/2013 | Panpaliya et al. |
| 8,401,275 B2 | 3/2013 | Wang et al. |
| 8,423,284 B2 | 4/2013 | O'Shea |
| 8,451,731 B1 | 5/2013 | Lee et al. |
| 8,463,435 B2 | 6/2013 | Herzog et al. |
| 8,503,340 B1 | 8/2013 | Xu |
| 8,515,577 B2 | 8/2013 | Wang et al. |
| 8,527,094 B2 | 9/2013 | Kumar et al. |
| 8,532,860 B2 | 9/2013 | Daly |
| 8,610,786 B2 | 12/2013 | Ortiz |
| 8,612,051 B2 | 12/2013 | Norman et al. |
| 8,639,797 B1 | 1/2014 | Pan et al. |
| 8,670,017 B2 | 3/2014 | Stuart et al. |
| 8,726,454 B2 | 5/2014 | Gilbert, Jr. et al. |
| 8,836,751 B2 | 9/2014 | Ballantyne et al. |
| 8,849,679 B2 | 9/2014 | Wang et al. |
| 8,849,680 B2 | 9/2014 | Wright et al. |
| 8,861,750 B2 | 10/2014 | Roe et al. |
| 8,897,920 B2 | 11/2014 | Wang et al. |
| 8,902,278 B2 | 12/2014 | Pinter et al. |
| 2001/0002448 A1 | 5/2001 | Wilson |
| 2001/0010053 A1 | 7/2001 | Ben-Shachar et al. |
| 2001/0020200 A1 | 9/2001 | Das et al. |
| 2001/0034475 A1 | 10/2001 | Flach et al. |
| 2001/0034544 A1 | 10/2001 | Mo |
| 2001/0037163 A1 | 11/2001 | Allard |
| 2001/0048464 A1 | 12/2001 | Barnett |
| 2001/0051881 A1 | 12/2001 | Filler |
| 2001/0054071 A1 | 12/2001 | Loeb |
| 2001/0055373 A1 | 12/2001 | Yamashita |
| 2002/0015296 A1 | 2/2002 | Howell et al. |
| 2002/0027597 A1 | 3/2002 | Sachau |
| 2002/0027652 A1 | 3/2002 | Paromtchik et al. |
| 2002/0033880 A1 | 3/2002 | Sul et al. |
| 2002/0038168 A1 | 3/2002 | Kasuga et al. |
| 2002/0044201 A1 | 4/2002 | Alexander et al. |
| 2002/0049517 A1 | 4/2002 | Ruffner |
| 2002/0055917 A1 | 5/2002 | Muraca |
| 2002/0057279 A1 | 5/2002 | Jouppi |
| 2002/0058929 A1 | 5/2002 | Green |
| 2002/0059587 A1 | 5/2002 | Cofano et al. |
| 2002/0063726 A1 | 5/2002 | Jouppi |
| 2002/0073429 A1 | 6/2002 | Beane et al. |
| 2002/0082498 A1 | 6/2002 | Wendt et al. |
| 2002/0085030 A1 | 7/2002 | Ghani |
| 2002/0095238 A1 | 7/2002 | Ahlin et al. |

(56) References Cited

U.S. PATENT DOCUMENTS

| | | |
|---|---|---|
| 2002/0095239 A1 | 7/2002 | Wallach et al. |
| 2002/0098879 A1 | 7/2002 | Rheey |
| 2002/0104094 A1 | 8/2002 | Alexander et al. |
| 2002/0106998 A1 | 8/2002 | Presley et al. |
| 2002/0109770 A1 | 8/2002 | Terada |
| 2002/0109775 A1 | 8/2002 | White et al. |
| 2002/0111988 A1 | 8/2002 | Sato |
| 2002/0120362 A1 | 8/2002 | Lathan et al. |
| 2002/0128985 A1 | 9/2002 | Greenwald |
| 2002/0130950 A1 | 9/2002 | James et al. |
| 2002/0133062 A1 | 9/2002 | Arling et al. |
| 2002/0141595 A1 | 10/2002 | Jouppi |
| 2002/0143923 A1 | 10/2002 | Alexander |
| 2002/0177925 A1 | 11/2002 | Onishi et al. |
| 2002/0183894 A1 | 12/2002 | Wang |
| 2002/0184674 A1 | 12/2002 | Xi et al. |
| 2002/0186243 A1 | 12/2002 | Ellis et al. |
| 2003/0021107 A1 | 1/2003 | Howell et al. |
| 2003/0030397 A1 | 2/2003 | Simmons |
| 2003/0048481 A1 | 3/2003 | Kobayashi et al. |
| 2003/0050733 A1 | 3/2003 | Wang et al. |
| 2003/0050734 A1 | 3/2003 | Lapham |
| 2003/0060808 A1 | 3/2003 | Wilk |
| 2003/0063600 A1 | 4/2003 | Noma et al. |
| 2003/0069752 A1 | 4/2003 | Ledain et al. |
| 2003/0080901 A1 | 5/2003 | Piotrowski |
| 2003/0100892 A1 | 5/2003 | Morley et al. |
| 2003/0104806 A1 | 6/2003 | Ruef et al. |
| 2003/0112823 A1 | 6/2003 | Collins et al. |
| 2003/0114962 A1 | 6/2003 | Niemeyer et al. |
| 2003/0120714 A1 | 6/2003 | Wolff et al. |
| 2003/0126361 A1 | 7/2003 | Slater et al. |
| 2003/0135097 A1 | 7/2003 | Wiederhold et al. |
| 2003/0135203 A1 | 7/2003 | Wang et al. |
| 2003/0144579 A1 | 7/2003 | Buss |
| 2003/0144649 A1 | 7/2003 | Ghodoussi et al. |
| 2003/0151658 A1 | 8/2003 | Smith |
| 2003/0152145 A1 | 8/2003 | Kawakita |
| 2003/0171710 A1 | 9/2003 | Bassuk et al. |
| 2003/0174285 A1 | 9/2003 | Trumbull |
| 2003/0180697 A1 | 9/2003 | Kim et al. |
| 2003/0195662 A1 | 10/2003 | Wang et al. |
| 2003/0199000 A1 | 10/2003 | Valkirs et al. |
| 2003/0206242 A1 | 11/2003 | Choi et al. |
| 2003/0212472 A1 | 11/2003 | McKee |
| 2003/0216833 A1 | 11/2003 | Mukai et al. |
| 2003/0216834 A1 | 11/2003 | Allard |
| 2003/0220541 A1 | 11/2003 | Salisbury et al. |
| 2003/0220715 A1 | 11/2003 | William et al. |
| 2003/0231244 A1 | 12/2003 | Bonilla et al. |
| 2003/0232649 A1 | 12/2003 | Gizis |
| 2003/0236590 A1 | 12/2003 | Park et al. |
| 2004/0001197 A1 | 1/2004 | Ko et al. |
| 2004/0001676 A1 | 1/2004 | Colgan et al. |
| 2004/0008138 A1 | 1/2004 | Hockley et al. |
| 2004/0010344 A1 | 1/2004 | Hiratsuka |
| 2004/0012362 A1 | 1/2004 | Tsurumi |
| 2004/0013295 A1 | 1/2004 | Sabe et al. |
| 2004/0017475 A1 | 1/2004 | Akers et al. |
| 2004/0019406 A1 | 1/2004 | Wang et al. |
| 2004/0024490 A1 | 2/2004 | McLurkin et al. |
| 2004/0041904 A1 | 3/2004 | Lapalme et al. |
| 2004/0065073 A1 | 4/2004 | Nash |
| 2004/0068657 A1 | 4/2004 | Alexander et al. |
| 2004/0078219 A1 | 4/2004 | Kaylor et al. |
| 2004/0080610 A1 | 4/2004 | James et al. |
| 2004/0088077 A1 | 5/2004 | Jouppi et al. |
| 2004/0088078 A1 | 5/2004 | Jouppi et al. |
| 2004/0093409 A1 | 5/2004 | Thompson et al. |
| 2004/0095516 A1 | 5/2004 | Rohlicek |
| 2004/0098167 A1 | 5/2004 | Yi et al. |
| 2004/0102167 A1 | 5/2004 | Shim et al. |
| 2004/0107254 A1 | 6/2004 | Ludwig et al. |
| 2004/0107255 A1 | 6/2004 | Ludwig et al. |
| 2004/0117065 A1 | 6/2004 | Wang et al. |
| 2004/0117067 A1 | 6/2004 | Jouppi |
| 2004/0123158 A1 | 6/2004 | Roskind |
| 2004/0135879 A1 | 7/2004 | Stacy et al. |
| 2004/0138547 A1 | 7/2004 | Wang et al. |
| 2004/0143421 A1 | 7/2004 | Wang et al. |
| 2004/0148638 A1 | 7/2004 | Weisman et al. |
| 2004/0150725 A1 | 8/2004 | Taguchi |
| 2004/0153211 A1 | 8/2004 | Kamoto et al. |
| 2004/0157612 A1 | 8/2004 | Kim |
| 2004/0162637 A1 | 8/2004 | Wang et al. |
| 2004/0167666 A1 | 8/2004 | Wang et al. |
| 2004/0167668 A1 | 8/2004 | Wang et al. |
| 2004/0168148 A1 | 8/2004 | Goncalves et al. |
| 2004/0170300 A1 | 9/2004 | Jouppi |
| 2004/0172301 A1 | 9/2004 | Mihai et al. |
| 2004/0172306 A1 | 9/2004 | Wohl et al. |
| 2004/0174129 A1 | 9/2004 | Wang et al. |
| 2004/0175684 A1 | 9/2004 | Kaasa et al. |
| 2004/0179714 A1 | 9/2004 | Jouppi |
| 2004/0186623 A1 | 9/2004 | Dooley et al. |
| 2004/0189700 A1 | 9/2004 | Mandavilli et al. |
| 2004/0201602 A1 | 10/2004 | Mody et al. |
| 2004/0205664 A1* | 10/2004 | Prendergast .................. 715/530 |
| 2004/0215490 A1 | 10/2004 | Duchon et al. |
| 2004/0218099 A1 | 11/2004 | Washington |
| 2004/0222638 A1 | 11/2004 | Bednyak |
| 2004/0224676 A1 | 11/2004 | Iseki |
| 2004/0230340 A1 | 11/2004 | Fukuchi et al. |
| 2004/0241981 A1 | 12/2004 | Dothan et al. |
| 2004/0260790 A1 | 12/2004 | Balloni et al. |
| 2005/0003330 A1 | 1/2005 | Asgarinejad et al. |
| 2005/0004708 A1 | 1/2005 | Goldenberg et al. |
| 2005/0007445 A1 | 1/2005 | Foote et al. |
| 2005/0013149 A1 | 1/2005 | Trossell |
| 2005/0021182 A1 | 1/2005 | Wang |
| 2005/0021183 A1 | 1/2005 | Wang et al. |
| 2005/0021187 A1 | 1/2005 | Wang et al. |
| 2005/0021309 A1 | 1/2005 | Alexander et al. |
| 2005/0024485 A1 | 2/2005 | Castles et al. |
| 2005/0027567 A1 | 2/2005 | Taha |
| 2005/0027794 A1 | 2/2005 | Decker |
| 2005/0028221 A1 | 2/2005 | Liu et al. |
| 2005/0035862 A1 | 2/2005 | Wildman et al. |
| 2005/0038416 A1 | 2/2005 | Wang et al. |
| 2005/0038564 A1 | 2/2005 | Burick et al. |
| 2005/0049898 A1 | 3/2005 | Hirakawa |
| 2005/0052527 A1 | 3/2005 | Remy et al. |
| 2005/0060211 A1 | 3/2005 | Xiao et al. |
| 2005/0065435 A1 | 3/2005 | Rauch et al. |
| 2005/0065438 A1 | 3/2005 | Miller |
| 2005/0065659 A1 | 3/2005 | Tanaka |
| 2005/0065813 A1 | 3/2005 | Mishelevich et al. |
| 2005/0071046 A1 | 3/2005 | Miyazaki et al. |
| 2005/0073575 A1 | 4/2005 | Thacher et al. |
| 2005/0075544 A1* | 4/2005 | Shapiro et al. ................ 600/300 |
| 2005/0078816 A1 | 4/2005 | Sekiguchi et al. |
| 2005/0083011 A1 | 4/2005 | Yang et al. |
| 2005/0099493 A1 | 5/2005 | Chew |
| 2005/0104964 A1 | 5/2005 | Bovyrin et al. |
| 2005/0110867 A1 | 5/2005 | Schulz |
| 2005/0122390 A1 | 6/2005 | Wang et al. |
| 2005/0125083 A1 | 6/2005 | Kiko |
| 2005/0125098 A1 | 6/2005 | Wang et al. |
| 2005/0149364 A1 | 7/2005 | Ombrellaro |
| 2005/0152447 A1 | 7/2005 | Jouppi et al. |
| 2005/0152565 A1 | 7/2005 | Jouppi et al. |
| 2005/0154265 A1 | 7/2005 | Miro et al. |
| 2005/0168568 A1 | 8/2005 | Jouppi |
| 2005/0182322 A1 | 8/2005 | Grispo |
| 2005/0192721 A1 | 9/2005 | Jouppi |
| 2005/0204438 A1 | 9/2005 | Wang et al. |
| 2005/0212478 A1 | 9/2005 | Takenaka |
| 2005/0219356 A1 | 10/2005 | Smith et al. |
| 2005/0225634 A1 | 10/2005 | Brunetti et al. |
| 2005/0231156 A1 | 10/2005 | Yan |
| 2005/0231586 A1 | 10/2005 | Rodman et al. |
| 2005/0232647 A1 | 10/2005 | Takenaka |
| 2005/0234592 A1 | 10/2005 | McGee et al. |
| 2005/0264649 A1 | 12/2005 | Chang et al. |

(56) References Cited

U.S. PATENT DOCUMENTS

| | | |
|---|---|---|
| 2005/0267826 A1 | 12/2005 | Levy et al. |
| 2005/0283414 A1 | 12/2005 | Fernandes et al. |
| 2005/0286759 A1 | 12/2005 | Zitnick et al. |
| 2006/0007943 A1 | 1/2006 | Fellman |
| 2006/0010028 A1 | 1/2006 | Sorensen |
| 2006/0013263 A1 | 1/2006 | Fellman |
| 2006/0013469 A1 | 1/2006 | Wang et al. |
| 2006/0013488 A1 | 1/2006 | Inoue |
| 2006/0014388 A1 | 1/2006 | Lur et al. |
| 2006/0020694 A1 | 1/2006 | Nag et al. |
| 2006/0029065 A1 | 2/2006 | Fellman |
| 2006/0047365 A1 | 3/2006 | Ghodoussi et al. |
| 2006/0048286 A1 | 3/2006 | Donato |
| 2006/0052676 A1 | 3/2006 | Wang et al. |
| 2006/0052684 A1 | 3/2006 | Takahashi et al. |
| 2006/0056655 A1 | 3/2006 | Wen et al. |
| 2006/0056837 A1 | 3/2006 | Vapaakoski |
| 2006/0064212 A1 | 3/2006 | Thorne |
| 2006/0066609 A1 | 3/2006 | Iodice et al. |
| 2006/0071797 A1 | 4/2006 | Rosenfeld et al. |
| 2006/0074525 A1 | 4/2006 | Close et al. |
| 2006/0074719 A1 | 4/2006 | Horner |
| 2006/0082642 A1 | 4/2006 | Wang et al. |
| 2006/0087746 A1 | 4/2006 | Lipow |
| 2006/0095158 A1 | 5/2006 | Lee et al. |
| 2006/0095170 A1 | 5/2006 | Yang et al. |
| 2006/0098573 A1 | 5/2006 | Beer et al. |
| 2006/0103659 A1 | 5/2006 | Karandikar et al. |
| 2006/0104279 A1 | 5/2006 | Fellman et al. |
| 2006/0106493 A1 | 5/2006 | Niemeyer et al. |
| 2006/0122482 A1 | 6/2006 | Mariotti et al. |
| 2006/0125356 A1 | 6/2006 | Meek et al. |
| 2006/0142983 A1 | 6/2006 | Sorensen et al. |
| 2006/0149418 A1 | 7/2006 | Anvari |
| 2006/0161136 A1 | 7/2006 | Anderson et al. |
| 2006/0161303 A1 | 7/2006 | Wang et al. |
| 2006/0164546 A1 | 7/2006 | Adachi et al. |
| 2006/0171515 A1 | 8/2006 | Hintermeister et al. |
| 2006/0173708 A1 | 8/2006 | Vining et al. |
| 2006/0173712 A1 | 8/2006 | Joubert |
| 2006/0178559 A1 | 8/2006 | Kumar et al. |
| 2006/0178776 A1 | 8/2006 | Feingold et al. |
| 2006/0178777 A1 | 8/2006 | Park et al. |
| 2006/0189393 A1 | 8/2006 | Edery |
| 2006/0195569 A1 | 8/2006 | Barker |
| 2006/0224405 A1* | 10/2006 | White .................. G06F 19/328 705/2 |
| 2006/0224781 A1 | 10/2006 | Tsao et al. |
| 2006/0247045 A1 | 11/2006 | Jeong et al. |
| 2006/0259193 A1 | 11/2006 | Wang et al. |
| 2006/0268704 A1 | 11/2006 | Ansari et al. |
| 2006/0271238 A1 | 11/2006 | Choi et al. |
| 2006/0271400 A1 | 11/2006 | Clements et al. |
| 2006/0293788 A1 | 12/2006 | Pogodin |
| 2007/0021871 A1 | 1/2007 | Wang et al. |
| 2007/0025711 A1 | 2/2007 | Marcus |
| 2007/0046237 A1 | 3/2007 | Lakshmanan et al. |
| 2007/0050937 A1 | 3/2007 | Song et al. |
| 2007/0064092 A1 | 3/2007 | Sandbeg et al. |
| 2007/0078566 A1 | 4/2007 | Wang et al. |
| 2007/0093279 A1 | 4/2007 | Janik |
| 2007/0112700 A1 | 5/2007 | Den et al. |
| 2007/0116152 A1 | 5/2007 | Thesling |
| 2007/0117516 A1 | 5/2007 | Saidi et al. |
| 2007/0120965 A1 | 5/2007 | Sandberg et al. |
| 2007/0122783 A1 | 5/2007 | Habashi |
| 2007/0133407 A1 | 6/2007 | Choi et al. |
| 2007/0135967 A1 | 6/2007 | Jung et al. |
| 2007/0142964 A1 | 6/2007 | Abramson |
| 2007/0170886 A1 | 7/2007 | Plishner |
| 2007/0176060 A1 | 8/2007 | White et al. |
| 2007/0192910 A1 | 8/2007 | Vu et al. |
| 2007/0197896 A1 | 8/2007 | Moll et al. |
| 2007/0198128 A1 | 8/2007 | Ziegler et al. |
| 2007/0198130 A1 | 8/2007 | Wang et al. |
| 2007/0199108 A1 | 8/2007 | Angle et al. |
| 2007/0216347 A1 | 9/2007 | Kaneko et al. |
| 2007/0226949 A1 | 10/2007 | Hahm et al. |
| 2007/0250212 A1 | 10/2007 | Halloran et al. |
| 2007/0255706 A1 | 11/2007 | Iketani et al. |
| 2007/0262884 A1 | 11/2007 | Goncalves et al. |
| 2007/0273751 A1 | 11/2007 | Sachau |
| 2007/0290040 A1 | 12/2007 | Wurman et al. |
| 2007/0291109 A1 | 12/2007 | Wang et al. |
| 2007/0291128 A1 | 12/2007 | Wang et al. |
| 2008/0009969 A1 | 1/2008 | Bruemmer et al. |
| 2008/0011904 A1 | 1/2008 | Cepollina et al. |
| 2008/0027591 A1 | 1/2008 | Lenser et al. |
| 2008/0033641 A1 | 2/2008 | Medalia |
| 2008/0045804 A1 | 2/2008 | Williams |
| 2008/0051985 A1 | 2/2008 | D'Andrea et al. |
| 2008/0065268 A1 | 3/2008 | Wang et al. |
| 2008/0082211 A1 | 4/2008 | Wang et al. |
| 2008/0086241 A1 | 4/2008 | Phillips et al. |
| 2008/0091340 A1 | 4/2008 | Milstein et al. |
| 2008/0126132 A1* | 5/2008 | Warner et al. .................... 705/3 |
| 2008/0133052 A1 | 6/2008 | Jones et al. |
| 2008/0161969 A1 | 7/2008 | Lee et al. |
| 2008/0174570 A1 | 7/2008 | Jobs et al. |
| 2008/0201016 A1 | 8/2008 | Finlay |
| 2008/0201017 A1 | 8/2008 | Wang et al. |
| 2008/0215987 A1 | 9/2008 | Alexander et al. |
| 2008/0229531 A1 | 9/2008 | Takida |
| 2008/0232763 A1 | 9/2008 | Brady |
| 2008/0255703 A1 | 10/2008 | Wang et al. |
| 2008/0263451 A1 | 10/2008 | Portele et al. |
| 2008/0263628 A1 | 10/2008 | Norman et al. |
| 2008/0267069 A1 | 10/2008 | Thielman et al. |
| 2008/0269949 A1 | 10/2008 | Norman et al. |
| 2008/0281467 A1 | 11/2008 | Pinter |
| 2008/0306375 A1 | 12/2008 | Sayler et al. |
| 2009/0030552 A1 | 1/2009 | Nakadai et al. |
| 2009/0044334 A1 | 2/2009 | Parsell et al. |
| 2009/0049640 A1 | 2/2009 | Lee et al. |
| 2009/0055023 A1 | 2/2009 | Walters et al. |
| 2009/0070135 A1* | 3/2009 | Parida et al. .................... 705/2 |
| 2009/0086013 A1 | 4/2009 | Thapa |
| 2009/0102919 A1 | 4/2009 | Zamierowski et al. |
| 2009/0105882 A1 | 4/2009 | Wang et al. |
| 2009/0106679 A1 | 4/2009 | Anzures et al. |
| 2009/0122699 A1 | 5/2009 | Alperovitch et al. |
| 2009/0125147 A1 | 5/2009 | Wang et al. |
| 2009/0144425 A1 | 6/2009 | Marr et al. |
| 2009/0164255 A1 | 6/2009 | Menschik et al. |
| 2009/0164657 A1 | 6/2009 | Li et al. |
| 2009/0171170 A1 | 7/2009 | Li et al. |
| 2009/0177323 A1 | 7/2009 | Ziegler et al. |
| 2009/0177641 A1 | 7/2009 | Raghavan |
| 2009/0237317 A1 | 9/2009 | Rofougaran |
| 2009/0240371 A1 | 9/2009 | Wang et al. |
| 2009/0248200 A1 | 10/2009 | Root |
| 2009/0259339 A1 | 10/2009 | Wright et al. |
| 2010/0010672 A1 | 1/2010 | Wang et al. |
| 2010/0010673 A1 | 1/2010 | Wang et al. |
| 2010/0017046 A1 | 1/2010 | Cheung et al. |
| 2010/0019715 A1 | 1/2010 | Roe et al. |
| 2010/0026239 A1 | 2/2010 | Li et al. |
| 2010/0030578 A1 | 2/2010 | Siddique et al. |
| 2010/0051596 A1 | 3/2010 | Diedrick et al. |
| 2010/0063848 A1 | 3/2010 | Kremer et al. |
| 2010/0066804 A1 | 3/2010 | Shoemake et al. |
| 2010/0070079 A1 | 3/2010 | Mangaser et al. |
| 2010/0073490 A1 | 3/2010 | Wang et al. |
| 2010/0076600 A1 | 3/2010 | Cross et al. |
| 2010/0085874 A1 | 4/2010 | Noy et al. |
| 2010/0088232 A1* | 4/2010 | Gale ........................... 705/50 |
| 2010/0115418 A1 | 5/2010 | Wang et al. |
| 2010/0116566 A1 | 5/2010 | Ohm et al. |
| 2010/0131103 A1 | 5/2010 | Herzog et al. |
| 2010/0145479 A1 | 6/2010 | Griffiths |
| 2010/0157825 A1 | 6/2010 | Anderlind et al. |
| 2010/0171826 A1 | 7/2010 | Hamilton et al. |
| 2010/0191375 A1 | 7/2010 | Wright et al. |
| 2010/0228249 A1 | 9/2010 | Mohr et al. |

(56) References Cited

U.S. PATENT DOCUMENTS

| | | |
|---|---|---|
| 2010/0268383 A1 | 10/2010 | Wang et al. |
| 2010/0278086 A1 | 11/2010 | Pochiraju et al. |
| 2010/0286905 A1 | 11/2010 | Goncalves et al. |
| 2010/0301679 A1 | 12/2010 | Murray et al. |
| 2010/0323783 A1 | 12/2010 | Nonaka et al. |
| 2011/0022705 A1 | 1/2011 | Yellamraju et al. |
| 2011/0050841 A1 | 3/2011 | Wang et al. |
| 2011/0071675 A1 | 3/2011 | Wells et al. |
| 2011/0071702 A1 | 3/2011 | Wang et al. |
| 2011/0072114 A1 | 3/2011 | Hoffert et al. |
| 2011/0153198 A1 | 6/2011 | Kokkas et al. |
| 2011/0172822 A1 | 7/2011 | Ziegler et al. |
| 2011/0187875 A1 | 8/2011 | Sanchez et al. |
| 2011/0190930 A1 | 8/2011 | Hanrahan et al. |
| 2011/0193949 A1 | 8/2011 | Nambakam et al. |
| 2011/0195701 A1 | 8/2011 | Cook et al. |
| 2011/0213210 A1 | 9/2011 | Temby et al. |
| 2011/0218674 A1 | 9/2011 | Stuart et al. |
| 2011/0245973 A1 | 10/2011 | Wang et al. |
| 2011/0280551 A1 | 11/2011 | Sammon |
| 2011/0292193 A1 | 12/2011 | Wang et al. |
| 2011/0301759 A1 | 12/2011 | Wang et al. |
| 2011/0306400 A1 | 12/2011 | Nguyen |
| 2012/0023506 A1 | 1/2012 | Maeckel et al. |
| 2012/0036484 A1 | 2/2012 | Zhang et al. |
| 2012/0059946 A1 | 3/2012 | Wang |
| 2012/0072023 A1 | 3/2012 | Ota |
| 2012/0072024 A1 | 3/2012 | Wang et al. |
| 2012/0092157 A1 | 4/2012 | Tran |
| 2012/0095352 A1 | 4/2012 | Tran |
| 2012/0113856 A1 | 5/2012 | Krishnaswamy |
| 2012/0191246 A1 | 7/2012 | Roe et al. |
| 2012/0191464 A1 | 7/2012 | Stuart et al. |
| 2012/0203731 A1 | 8/2012 | Nelson et al. |
| 2012/0291809 A1 | 11/2012 | Kuhe et al. |
| 2013/0250938 A1 | 9/2013 | Anandakumar et al. |
| 2014/0047022 A1 | 2/2014 | Chan et al. |
| 2014/0085543 A1 | 3/2014 | Hartley et al. |
| 2014/0135990 A1 | 5/2014 | Stuart et al. |
| 2014/0139616 A1 | 5/2014 | Pinter et al. |
| 2014/0155755 A1 | 6/2014 | Pinter et al. |

FOREIGN PATENT DOCUMENTS

| | | |
|---|---|---|
| CN | 1404695 A | 3/2003 |
| CN | 1554193 A | 12/2004 |
| CN | 1554985 A | 12/2004 |
| CN | 1561923 A | 1/2005 |
| CN | 1743144 A | 3/2006 |
| CN | 101049017 A | 10/2007 |
| CN | 101106939 A | 1/2008 |
| CN | 101151614 A | 3/2008 |
| CN | 100407729 C | 7/2008 |
| CN | 101390098 A | 3/2009 |
| CN | 101507260 A | 8/2009 |
| CN | 101730894 A | 6/2010 |
| CN | 101866396 A | 10/2010 |
| CN | 101978365 A | 2/2011 |
| CN | 102203759 A | 9/2011 |
| CN | 101106939 B | 11/2011 |
| EP | 92/466492 A2 | 1/1992 |
| EP | 92/488673 A2 | 6/1992 |
| EP | 981905 B1 | 1/2002 |
| EP | 1262142 A2 | 12/2002 |
| EP | 1304872 A1 | 4/2003 |
| EP | 1536660 A3 | 9/2004 |
| EP | 1536660 A2 | 6/2005 |
| EP | 1573406 A2 | 9/2005 |
| EP | 2005/1594660 A2 | 11/2005 |
| EP | 1763243 A2 | 3/2007 |
| EP | 1791464 A2 | 6/2007 |
| EP | 1800476 A2 | 6/2007 |
| EP | 1819108 A2 | 8/2007 |
| EP | 1856644 A2 | 11/2007 |
| EP | 1928310 A2 | 6/2008 |
| EP | 1232610 B1 | 1/2009 |
| EP | 2027716 A2 | 2/2009 |
| EP | 2145274 A1 | 1/2010 |
| EP | 2214111 A2 | 8/2010 |
| EP | 2263158 | 12/2010 |
| EP | 2300930 | 3/2011 |
| EP | 2011/2342651 A2 | 7/2011 |
| GB | 2431261 A | 4/2007 |
| JP | 7-194609 A | 8/1995 |
| JP | 7213753 A | 8/1995 |
| JP | 7248823 A | 9/1995 |
| JP | 7257422 A | 10/1995 |
| JP | 8084328 A | 3/1996 |
| JP | 8320727 A | 12/1996 |
| JP | 9267276 A | 10/1997 |
| JP | 10079097 A | 3/1998 |
| JP | 10288689 A | 10/1998 |
| JP | 11-220706 A | 8/1999 |
| JP | 32319 A | 1/2000 |
| JP | 49800 A | 2/2000 |
| JP | 79587 A | 3/2000 |
| JP | 196876 A | 7/2000 |
| JP | 188124 A | 4/2001 |
| JP | 125641 A | 5/2001 |
| JP | 1147718 A | 5/2001 |
| JP | 179663 A | 7/2001 |
| JP | 1198865 A | 7/2001 |
| JP | 1198868 A | 7/2001 |
| JP | 1199356 A | 7/2001 |
| JP | 2000574 A | 1/2002 |
| JP | 46088 A | 2/2002 |
| JP | 235423 A | 2/2002 |
| JP | 2002/112970 A | 4/2002 |
| JP | 2002/101333 A | 5/2002 |
| JP | 2305743 A | 10/2002 |
| JP | 2002-321180 A | 11/2002 |
| JP | 2355779 A | 12/2002 |
| JP | 2004-181229 A | 7/2004 |
| JP | 524824 T | 8/2004 |
| JP | 261941 A | 9/2004 |
| JP | 2004/289379 A | 10/2004 |
| JP | 28066 A | 2/2005 |
| JP | 2005/059170 A | 3/2005 |
| JP | 2005-111083 A | 4/2005 |
| JP | 2006/508806 A | 3/2006 |
| JP | 2006/109094 A | 4/2006 |
| JP | 2006/224294 A | 8/2006 |
| JP | 2006/246438 A | 9/2006 |
| JP | 2007-7040 A | 1/2007 |
| JP | 2007/081646 A | 3/2007 |
| JP | 2007-232208 A | 9/2007 |
| JP | 2007-316966 A | 12/2007 |
| JP | 2009-125133 A | 6/2009 |
| JP | 2010/064154 A | 3/2010 |
| JP | 2010/532109 A | 9/2010 |
| JP | 246954 A | 11/2010 |
| KR | 2006/0037979 A | 5/2006 |
| KR | 2009/0012542 A | 2/2009 |
| KR | 19479 A | 2/2010 |
| KR | 139037 | 12/2010 |
| WO | 93/06690 A1 | 4/1993 |
| WO | 1997/42761 A1 | 11/1997 |
| WO | 51078 A1 | 11/1998 |
| WO | 67067 | 12/1999 |
| WO | 2000/025516 A1 | 5/2000 |
| WO | 33726 | 6/2000 |
| WO | 2001/031861 A1 | 5/2001 |
| WO | 77745 A1 | 9/2003 |
| WO | 2004/008738 A1 | 1/2004 |
| WO | 2004/012018 A2 | 2/2004 |
| WO | 75456 A2 | 9/2004 |
| WO | 2006/012797 A2 | 2/2006 |
| WO | 2006/078611 A1 | 4/2006 |
| WO | 2006044847 A2 | 4/2006 |
| WO | 2007/041295 A1 | 4/2007 |
| WO | 41295 A1 | 4/2007 |
| WO | 2007/041038 A1 | 6/2007 |
| WO | 2008/100272 A2 | 8/2008 |
| WO | 2008/100272 A3 | 10/2008 |

(56) References Cited

FOREIGN PATENT DOCUMENTS

| | | | |
|---|---|---|---|
| WO | 2009/117274 | A2 | 9/2009 |
| WO | 2009/128997 | A1 | 10/2009 |
| WO | 2009/145958 | A2 | 12/2009 |
| WO | 2010/006205 | A1 | 1/2010 |
| WO | 2010/006211 | A1 | 1/2010 |
| WO | 33666 | A1 | 3/2010 |
| WO | 2010/047881 | A1 | 4/2010 |
| WO | 2010/062798 | A1 | 6/2010 |
| WO | 2010/065257 | A1 | 6/2010 |
| WO | 120407 | A1 | 10/2010 |
| WO | 028589 | A2 | 3/2011 |
| WO | 2011/028589 | A3 | 4/2011 |
| WO | 2007/097132 | A2 | 8/2011 |
| WO | 97130 | A2 | 8/2011 |
| WO | 109336 | A2 | 9/2011 |
| WO | 2011/097132 | A3 | 12/2011 |
| WO | 2011/149902 | A2 | 12/2011 |

OTHER PUBLICATIONS

Ando, et al., "A Multimedia Self-service Terminal with Conferencing Functions", IEEE, Jul. 5-7, 1995, pp. 357-362.
Android Amusement Corp., "What Marketing Secret . . . Renting Robots from Android Amusement Corp!", (Advertisement), 1982.
Applebome, "Planning Domesticated Robots for Tomorrow's Household", New York Times, http://www.theoldrobots.com/images17/dc17.JPG, Mar. 4, 1982, 21 & 23.
Baltus, et al., "Towards Personal Service Robots for the Elderly, Proceedings for the Elderly Workshop on Interactive Robots and Entertainment", Computer Science and Robotics, 2000.
Bar-Cohen, et al., "Virtual reality robotic telesurgery simulations using MEMICA haptic system", Internet, Mar. 5, 2001, pp. 1-7.
Bartholomew, "An Apothecary's Pharmacy", http://classes.bnf.fr/ema/grands/034.htm, pp. 1230-1240.
Bauer, Jeffrey C. et al., "Service Robots in Health Care: The Evolution of Mechanical Solutions to Human Resource Problems", Jun. 2003.
Bauer, John et al., "Remote telesurgical mentoring: feasibility and efficacy", IEEE, 2000, pp. 1-9.
Bischoff, "Design Concept and Realization of the Humanoid Service Robot HERMES", Field and Service Robotics, Springer, London, 1998, pp. 485-492.
Blackwell, Gerry, "Video: A Wireless LAN Killer App?", Internet, Apr. 16, 2002, pp. 1-3.
Breslow, Michael J. et al., "Effect of a multiple-site intensive care unit telemedicine program on clinical and economic outcome An alternative paradigm for intensivist staffing", Critical Care Med; vol. 32 No. 1, Jan. 2004, pp. 31-38.
Brooks, Rodney, "Remote Presence", Abstracts from Flesh & Machines, How Robots Will Change Us, Feb. 2002, pp. 131-147.
Candelas, Herias et al., "Flexible virtual and remote laboratory for teaching Robotics", FORMATEX 2006; Proc. Advance in Control Education Madrid, Spain, Jun. 2006, pp. 21-23.
Celi et al., "The EICU: It's not just telemedicine", Critical Care Medicine vol. 29, No. 8 (Supplement), Aug. 2001.
Cheetham, Anastasia et al., "Interface Development for a Child's Video Conferencing Robot", 2000, pp. 1-4.
Cleary, et al., "State of the art in surgical robotics: Clinical applications and technology challenges", Internet, Feb. 24, 2002, pp. 1-26.
CNN, "Floating 'droids' to roam space corridors of the future", Internet, Jan. 12, 2000, pp. 1-4.
cnn.com/technology, "Paging R.Robot: Machine helps doctors with patients", Internet, Sep. 30, 2003, pp. 1-3.
Crowley, Susan L., "Hello to Our Future", AARP Bulletin, http://www.cs.cmu.ed/-nursebot/web/press/aarp 99_14/millennium.html, Jan. 2000.
Dalton, "Techniques for Web Telerobotics", PhD Thesis, University of Western Australia, http://telerobot.mech.uwa.edu.au/information.html, http://catalogue.library.uwa.edu.au/search, 2001, pp. 27-62.

Davies, "Robotics in Minimally Invasive Surgery", Internet, 1995, pp. 5/1-5/2.
Digiorgio, James, "Is Your Emergency Department of the Leading Edge?", Internet, 2005, pp. 1-4.
Elhajj, et al., "Supermedia in Internet-based telerobotic operations", Internet, 2001, pp. 1-14.
Elhajj, et al., "Synchronization and Control of Supermedia Transmission via the Internet", Proceedings of 2001 International Symposium on Intelligent Multimedia Video and Speech Processing., Hong Kong, May 2-4, 2001.
Ellison, et al., "Telerounding and Patient Satisfaction Following Surgery", pp. 523-530.
Fels, "Developing a Video-Mediated Communication System for Hospitalized Children", Telemedicine Journal, vol. 5, No. 2, 1999.
Fetterman, "Videoconferencing over the Internet", Internet, 2001, pp. 1-8.
Fiorini, "Health Care Robotics: A Progress Report", IEEE International Conference on Robotics and Automation, Apr. 1997, pp. 1271-1276.
Ghiasi, et al., "A Generic Web-based Teleoperations Architecture: Details and Experience", SPIE Conference on Telemanipulator and Telepresence Technologies VI, Sep. 1999.
Goldberg, et al., "Collaborative Teleoperation via the Internet", IEEE International Conference on Robotics and Automation, San Francisco, California, Apr. 2000.
Goldberg, "Desktop Teleoperation via the World Wide Web, Proceedings of the IEEE International Conference on Robotics and Automation", htto://citeseer.ist.osu.edu/cache/oaoers/cs/5/fto:zSzzSzusc.eduzSzoubzSziriszSzraiders.odf/aol, 1995, pp. 654-659.
Goldberg, "More Online Robots, Robots that Manipulate", Internet, Updated Aug. 2001, http://ford.ieor.berkeley.edu/ir/robots_a2.html.
Goldenberg, et al., "Telemedicine in Otolaryngology", American Journal of Otolaryngology vol. 23, No. 1, 2002, pp. 35-43.
Goldman, Lea, "Machine Dreams", Entrepreneurs, Forbes, May 27, 2002.
Gump, Michael D., "Robot Technology Improves VA Pharmacies", Internet, 2001, pp. 1-3.
Hameed, Mohammed et al., ""A Review of Telemedicine"", Journal of Telemedicine and Telecare., vol. 5, Supplement 1, 1999, pp. S1:103-S1:106.
Han, et al., "Construction of an Omnidirectional Mobile Robot Platform Based on Active Dual-Wheel Caster Mechanisms and Development of a Control Simulator", Kluwer Acedemic Publishers, vol. 29, Nov. 2000, pp. 257-275.
Handley, et al., "RFC 2327—SDP:Session Description Protocol", http://www.faqs.org/rfcs/rfc2327.html, Apr. 1998.
Hanebeck, et al., "ROMAN: a mobile Robotic Assistant for Indoor Service Applications", Proceedings of the 1997 IEEE/RSJ International Conference on Intelligent Robots and Systems, 1997.
Harmo, et al., "Moving Eye—Interactive Telepresence Over Internet With a Ball Shaped Mobile Robot", 2000.
Haule, et al., "Control Scheme for Delayed Teleoperation Tasks", Proceedings of the Pacific Rim Conference on Communications, Computer and Signal Processing, May 17, 1995.
Hees, William P., "Communications Design for a Remote Presence Robot", Jan. 14, 2002.
Holmberg, "Development of a Holonomic Mobile Robot for Mobile Manipulation Tasks", International Conference on Field and Service Robotics, Pittsburgh, PA, Aug. 1999.
"Inventing the Future: 2000 Years of Discovery", Discovery Channel Canada, (VideoITranscript), Jan. 2, 2000.
Ishiguro, "Integrating a Perceptual Information Infrastructure with Robotic Avatars: A Framework for Tele-Existence", Proceeding of IEEE Conference on Intelligent Robots and Systems, 1999, pp. 1032-1038.
Ishihara, et al., "Intelligent Microrobot DDS (Drug Delivery System) Measured and Controlled by Ultrasonics", IEEE/RSJ, vol. 2, Nov. 3-5, 1991, pp. 1145-115.
"ITU-T H.323 Packet-based multimedia communications", ITU, http://www.itu.int/rec/T-REC-H.323-199802-S/en, Feb. 1998.
Ivanova, Natali, "Master's thesis: Internet Based Interface for Control of a Mobile Robot", Department of Numerical Analysis and Computer Science, 2003, 59 pages.

(56) References Cited

OTHER PUBLICATIONS

Jenkins, et al., "Telehealth Advancing Nursing Practice", Nursing Outlook, vol. 49, No. 2, Mar./Apr. 2001.
Johanson, "Supporting video-mediated communication over the Internet", Chalmers University of Technology, Dept of Computer Engineering, Gothenburg, Sweden, 2003.
Jouppi, et al., "Mutually-Immersive Audio Telepresence", Audio Engineering Society Convention Paper presented at 113th Convention, Oct. 2002.
Jouppi, Norman et al., "First Steps Towards Mutually-Immersive Mobile Telepresence", CSCW, 02, New Orleans LA, Nov. 16-20, 2002.
Kanehiro, Fumio et al., "Virtual Humanoid Robot Platform to Develop Controllers of Real Humanoid Robots without Porting", IEEE, 2001, pp. 3217-3276.
Kaplan, A. E. et al., "An Internet Accessible Telepresence", {aek keshav nls jhv}@research.att.com, AT&T Bell Laboratories, Murray Hill, N.J., pp. 1-7.
Keller, et al., "Raven Interface Project", Fall 2001, http://upclose.lrdc.pitt.edu/people/louwassets/RavenSlides.pps.
Khatib, "Robots in Human Environments", Proc. International Conference on Control, Automation, Robotics, and Vision ICRACV2000, Singapore, Dec. 2000, pp. 454-457.
Kuzuoka, et al., "Can the GestureCam Be a Surrogate?", Proceedings of the Fourth European Conference on Computer-Supported Cooperative Work, Sep. 10-14, pp. 181-196.
Lane, "Automated Aides", Newsday, http://www.cs.cum.edu/nursebot/web/press/nd4380.htm, Oct. 17, 2000.
Lee, et al., "A novel method of surgical instruction: International telementoring", Internet, 1998, pp. 1-4.
Lim, Hun-Ok et al., "Control to Realize Human-like Walking of a Biped Humanoid Robot", IEEE, 2000, pp. 3271-3276.
Linebarger, John M. et al., "Concurrency Control Mechanisms for Closely Coupled Collaboration in Multithreaded Virtual Environments", Presence, Special Issue on Advances in Collaborative VEs, 2004.
Loeb, et al., "Virtual Visit: Improving Communication for Those Who Need It Most", Stud Health Technol Inform.; 94: pp. 302-308., 2003.
Long, "HelpMate Robotics, Inc. (Formerly Transitions Research Corporation) Robot Navigation Technology", NIST Special Publication, http://www.atp.nist.gov/eao/sp950-1/helpmate.htm, Mar. 1999, pp. 950-951.
Luna, Nancy, "Robot a new face on geriatric care", OC Register, Aug. 6, 2003.
Mack, "Minimally invasive and robotic surgery", Internet IEEE, 2001, pp. 568-572.
Mair, "Telepresence—The Technology. And Its Economic and Social Implications", IEEE Technology and Society, 1997.
Martin, Anya, "Days Ahead", Assisted Living Today, vol. 9, Nov./Dec. 2002, pp. 19-22.
Mccardle, et al., "The challenge of utilizing new technology in design education", Internet, 2000, pp. 122-127.
Meng, et al., "E-Service Robot in Home Healthcare", Proceedings of the 2000 IEEE/RSJ, International Conference on Intelligent Robots and Systems, 2000, pp. 832-837.
Michaud, "Introducing Nursebot", The Boston Globe, http://www.cs.cmu.edu/nursebot/web/press/globe 3 01/index.html, Sep. 11, 2001, pp. 1-5.
Montemerlo, "Telepresence: Experiments in Next Generation Internet", CMU Robotics Institute, http://www.ri.cmu.edu/creative/archives.htm (Video/Transcript), Oct. 20, 1998.
Murphy, "Introduction to AI Robotics", A Bradford Book, 2000, 487.
Nakajima, et al., "A Multimedia Teleteaching System using an Electronic Whiteboard for Two Way Communication of Motion Videos and Chalkboards", IEEE, 1993, pp. 436-441.
"National Energy Research Scientific Computing Center, Berkeley Lab's RAGE Telepresence Robot Captures R&D100 Award", http://www.nersc.gov/news/newsroom/RAGE070202.php, Jul. 2, 2002.
"Nomad XR4000 Hardware Manual", Nomadic Technologies, Inc., Mar. 1999.
Ogata, et al., "Development of Emotional Communication Robot: WAMOEBA-2r—Experimental evaluation .", IEEE, 2000, pp. 175-180.
Ogata, et al., "Emotional Communication Robot: WAMOEBA-2R—Emotion Model and Evaluation Experiments", Internet, 1999, pp. 1-16.
Oh, et al., "Autonomous Battery Recharging for Indoor Mobile Robots", Proceedings of Australian Conference on Robotics and Automation, http://users.rsise.anu.edu.au/rsl/rsl_papers/ACRA2000/Auto_Recharge_Paper.pdf, 2000.
Ojha, A. K., "An application of Virtual Reality in Rehabilitation", IEEE, Apr. 10-13, 1994, pp. 4-6.
Paulos, et al., "A World Wide Web Telerobotic Remote Environment Browser", http://vive.cs.berkeley.edu/capek, 1995.
Paulos, "Designing Personal Tele-embodiment", IEEE International Conference on Robotics and Automation http://www.prop.org/papers/icra98.pdf, 1998.
Paulos, "PRoP: Personal Roving Presence", ACM:CHI Proceedings of CHI '98, http://www.prop.org/papers/chi98.pdf, 1998, p. 6.
Paulos, et al., "Ubiquitous Tele-embodiment: Applications and Implications", International Journal of Human Computer Studies, vol. 46, No. 6, Jun. 1997, pp. 861-877.
Paulos, "Video of PRoP 2 at Richmond Field Station", www.prop.org Printout of Home Page of Website and two-page Transcript of the audio portion of said PRoP Video, May 2001.
Paulos, Eric J., "Personal Tele-Embodiment", UC Berkeley, Fall 2001.
Pin, et al., "A New Family of Omnidirectional and Holonomic Wheeled Platforms for Mobile Robots", IEEE, vol. 10, No. 4, Aug. 1994.
Rovetta, et al., "A New Telerobotic Application: Remote Laparoscopic Surgery Using Satellites and and optical fiber Networks for Data Exchange", International Journal of Robotics Research, Jun. 1, 1996, pp. 267-279.
Roy, et al., "Towards Personal Service Robots for the Elderly", Internet, Mar. 7, 2002, 7 pgs.
Salemi, et al., "MILO: Personal robot platform", Internet, 2005, pp. 1-6.
Sandt, Frederic et al., "Perceptions for a Transport Robot in Public Environments", IROS, 1997.
Schaeffer, "Care-O-bot: A System for Assisting Elderly or Disabled Persons in Home Environments", Proceedings of AAATE-99, http://morpha.de/download/publications/IPA, 1999.
Schulz, "Web Interfaces for Mobile Robots in Public Places", Robotics & Automation Magazine, IEEE, vol. 7, Issue 1, Mar. 2000.
Shimoga, et al., "Touch and force reflection for telepresence surgery", IEEE, 1994, pp. 1049-1050.
Siegwart, "Interacting Mobile Robots on the Web", Proceedings of the 1999 IEEE International Conference on Robotics and Automation, May 1999.
Simmons, "Xavier: An Autonomous Mobile Robot on the Web", IEEE Robotics and Automation Magazine, 1999, pp. 43-48.
"Spawar Systems Center, "Robart"", San Diego, CA, http://web.archive.org/web/*/http://www.nosc.mil/robots/land/robart/robart.html, 1998.
Stephenson, Gary, "Dr. Robot Tested at Hopkins", Internet, Aug. 5, 2003, pp. 1-2.
Stoianovici, et al., "Robotic Tools for Minimally Invasive Urologic Surgery", Internet, Dec. 2002, pp. 1-17.
Suplee, "Mastering the Robot", The Washington Post, http://www.cs.cmu.edu-nursebotlweb/press/wash/index.html, Sep. 17, 2000, p. A01.
Tahboub, Karim A. et al., "Dynamics Analysis and Control of a Holonomic Vehicle With Continously Variable Transmission", Journal of Dynamic Systems, Measurement and Control ASME vol. 124, Mar. 2002, pp. 118-126.
Tendick, et al., "Human-Machine Interfaces for Minimally Invasive Surgery", IEEE, 1997, pp. 2771-2776.
Thrun, et al., "Probabilistic Algorithms and the Interactive Museum Tour-Guide Robot Minerva", Internet, 2000, pp. 1-35.

(56) References Cited

OTHER PUBLICATIONS

Tzafestas, et al., "VR-based Teleoperation of a Mobile Robotic Assistant: Progress Report", Internet, Nov. 2000, pp. 1-23.
Urquhart, Kim , "InTouch's robotic Companion 'beams up' healthcare experts", Medical Device Daily, vol. 7, No. 39, Feb. 27, 2003, p. 1,4.
Weiss, et al., "Telework and video-mediated communication: Importance of real-time, interactive communication for workers with disabilities", California State University Northridge http://www.csun.edu/cod/conf/1999/proceedings/session0238.html, pp. 1-4.
West, et al., "Design of Ball Wheel Mechanisms for Omnidirectional Vehicles with Full Mobility and Invariant Kinematics", Journal of Mechanical Design , vol. 119, Jun. 1997, pp. 153-161.
Yamasaki, et al., "Applying Personal Robots and Active Interface to Video Conference Systems", Internet, 1995, pp. 243-248.
Yamauchi, "PackBot: A Versatile Platform for Military Robotics", Internet, 2004, pp. 1-10.
Yong, et al., "Robot task execution with telepresence using virtual reality technology", Internet, 1998, pp. 1-8.
Zamrazil, Kristie, "Telemedicine in Texas: Public Policy Concerns", House Research Organization Focus Report, Texas House of Representatives, http://www.hro.house.state.tx.us/focus/telemed.pdf, May 5, 2000, pp. 76-22.
Zipperer, Lorri, "Robotic dispensing system", 1999, pp. 1-2.
Zorn, Benjamin G., "Ubiquitous Telepresence", http://www.cs.colorado.edu/-zorn/utlvision/vision.html, May 5, 1996.
Barrett, "Video Conferencing Business Soars as Companies Cut Travel; Some Travel Cuts Are Permanent", http://www.ivci.com/international_videoconferencing_news_videoconferencing_news_19.html, Mar. 13, 2002.
Brooks, "A Robust Layered Control System for a Mobile Robot," IEEE Journal of Robotics and Automation, 2 (1), Mar. 1986, 10 pgs.
Davis, "Meet iRobot, The Smartest Webcam on Wheels," Wired Magazine, 8.09, http://www.wired.com/wired/archive/8.09/irobot_pr.html, Sep. 2000, 2 pgs.
Dean, et al., "1992 AAAI Robot Exhibition and Competition," AI Magazine, Spring 1993, 10 pgs.
"Defendant VGo Communications, Inc.'s Invalidity Contentions Pursuant to the Feb. 27, 2012 Civil Minute Order", May 2, 2012.
"Defendant-Counterclaimant VGo Communications, Inc.'s Supplemental Invalidity Contentions Pursuant to the Feb. 27, 2012 Civil Minute Order", May 14, 2012.
Dudenhoeffer, et al., "Command and Control Architectures for Autonomous Micro-Robotic Forces", http://www.inl.gov/technicalpublications/Documents/3157051.pdf, Apr. 2001.
Elhajj, "Real-Time Haptic Feedback in Internet-Based Telerobotic Operation", IEEE International Conference on Electro/Information Technology, http://www.egr.msu.edu/~ralab-web/cgi_bin/internet-teleoperation.php, Jun. 2000.
Fong, "Collaborative Control: A Robot-Centric Model for Vehicle Teleoperation", The Robotics Institute Carnegie Mellon University, http://web.archive.org/web/20030504040803/www.ricmu.edu/cgi-bin/tech_reports.cgi?year=2001&text=0, Nov. 2001.
Grow, "Office Coworker Robot," Time Magazine, http://www.time.com/time/specials/packages/article/0,28804,1936165_1936255_1936640,00.html, Nov. 19, 2001, 2 pgs.
ITU, "ITU-T H.281 A Far End Camera Control Protocol for Videoconferences using H.224", http://www.itu.int/rec/T-RECH.281-199411-1/en, Nov. 1994.
ITU, "ITU-T H.450.11 Call Intrusion Supplementary Service for H.323", http://www.itu.int/rec/T-RECH.450.11-200103-1/en, Mar. 2001.
ITU, "ITU-T H.450.9 Call Completion Supplementary Services for H.323", http://www.itu.int/rec/T-RECH.450.9-200011-1/en, Nov. 2000.
Knight, et al., "Active Visual Alignment of a Mobile Stereo Camera Platform", Proceedings of the IEEE, International Conference on Robotics and Automation, San Francisco, Apr. 24-28, 2000, pp. 3202-3208.
Metz, "HP Labs", PCMAG.com, http://www.pcmag.com/article2/0,2817,1130820,00.asp, Jul. 1, 2003.
"PictureTel Adds New Features and Functionality to Its Award-Winning Live200 Desktop Videoconferencing System", PR Newswire Association, LLC, Gale, Cengage Learning, http://www.thefreelibrary.com/PictureTel+Adds+New+Features+And+Functionality+To+Its+Award-Winning...-a019512804, Jun. 13, 1997.
Picturetel, "PictureTel Live200 for Windows NT Product Guide", http://support.polycom.com/global/documents/support/user/products/video/live200_live200NT_product_guide.pdf, Nov. 1994.
Roach, "Automatic Call Back Service in SIP", http://tools.ietf.org/pdf/draftroach-sip-acb-00.pdf, Mar. 2000.
Summers, "Microsoft NetMeeting 3 Features excerpt from Official Microsoft NetMeeting 3.0 Book", http://technet.microsoft.com/en-us/library/cc723477.aspx#XSLTsection121121120120, excerpt from Microsoft Press http://www.computerbooksonline.com/abook.asp?i=0735605823, Mar. 1999.
U.S. Appl. No. 10/783,760, filed Feb. 20, 2004, Wang, et al., 48 pgs.
U.S. Appl. No. 60/449,762, filed Feb. 24, 2003, Wang, et al., 28 pgs.
Weiss, et al., "PEBBLES: A Personal Technology for Meeting Education, Social and Emotional Needs of Hospitalised Children", Personal and Ubiquitous Computing 5, Springer-Verlag London Ltd., 2001, pp. 157-168.
Zambroski, "CMU, Pitt Developing 'nursebot'", http://www.cs.cmu.edu/~nursebot/web/press/tribunereview.html, Oct. 27, 2000.
Dario et al., "A Robot Workstation for Diagnosis and Physical Therapy", IEEE Catalog No. 88TH0234-5, 1988, pp. 67-72.
Koenen, Rob, "MPEG-4: a Powerful Standard for Use in Web and Television Environments", KPN Research, Available Online at <http://www.w3.org/Architecture/1998/06/Workshop/paper26>, Retrieved on Jun. 25, 2014, 4 pages.
Library of Congress, "008—Fixed-Length Data Elements (NR)", MARC 21 Format for Classification Data, Available Online at <http://www.loc.gov/marc/classification/cd008.html>, Jan. 2000, 13 pages.
Noritsugu et al., "Application of Rubber Artificial Muscle Manipulator as a Rehabilitation Robot", Mechatronics, IEEE/ASME Transactions, vol. 2, No. 4, Dec. 1997, pp. 259-267.
Panusopone et al., "Performance Comparison of MPEG-4 and H.263+ for Streaming Video Applications", Circuits Systems Signal Processing, vol. 20, No. 3, 2001, pp. 293-309.
Paulos, Eric John, "Personal Tele-Embodiment", Electrical Engineering and Computer Sciences, 2001, 25 pages.
Paulos et al., "Personal Tele-Embodiment", Chapter 9 in Goldberg et al., ed. "Beyond Webcams", MIT Press, 2002, 21 pages.
Paulos, Eric John, "Personal Tele-Embodiment", OskiCat UCB Library Catalog, Available Online at <http://oskicat.berkeley.edu/search-S 1 ?/Xpersonal+tele-embodim . . . >, 2001, 3 pages.
Paulos et al., "Social Tele-Embodiment: Understanding Presence", Autonomous Robots, vol. 11, No. 1, Kluwer Academic Publishers, 2001, pp. 87-95.
Schraft et al., "Care-O-bot™: the Concept of a System for Assisting Elderly or Disabled Persons in Home Environments", IEEE Proceedings of the 24th Annual Conference of the Industrial Electronics Society, IECON '98, Aug. 31-Sep. 4, 1998, pp. 2476-2481.
Weaver et al., "Monitoring and Controlling Using the Internet and Java", Proceedings of the 25th Annual Conference of the IEEE Industrial Electronics Society, vol. 3, 1999, pp. 1152-1158.
Google translation of: Innovations Report, From Research Project to Television Star: Care-O-bot in ZDF series, Available Online at <http://www.innovations-report.de/specials/printa.php?id=5157>, Sep. 28, 2001, 2 pages.
Screenshot Showing Google Date for Lemaire Telehealth Manual, Screenshot Retrieved, Available Online at <https://www.google.co.in/webhp?sourceid=chrome-instant&ion=1&espv=2&ie=UTF-8#q=Lemaire+Telehealth+Manual>, retrieved on Dec. 18, 2014, 2 pages.
Appeal from the U.S. District Court for the Central District of California in case No. 11-cv-9185, Judge Percy Anderson, Joint Appendix, vol. I of IV, Jun. 24, 2013, pp. A1-A6357.
Appeal from the U.S. District Court for the Central District of California in case No. 11-cv-9185, Judge Percy Anderson, Joint Appendix, vol. II of IV, Jun. 24, 2013, pp. A6849-A10634.
Appeal from the U.S. District Court for the Central District of California in case No. 11-cv-9185, Judge Percy Anderson, Joint Appendix, vol. III of IV, Jun. 24, 2013, pp. A10654-A15517.

(56) References Cited

OTHER PUBLICATIONS

Appeal from the U.S. District Court for the Central District of California in case No. 11-cv-9185, Judge Percy Anderson, Joint Appendix, vol. IV of IV, Jun. 24, 2013, pp. A15677-A18127.

Appeal from the U.S. District Court for the Central District of California in No. 11-CV-9185, Judge Percy Anderson, May 9, 2014, pp. 1-48.

Civil Minutes—General: Case No. CV 11-9185PA (AJWx), *InTouch Tech., Inc.* v. *VGO Commons, Inc.*, Sep. 10, 2012, 7 pages.

"Magne Charge", Smart Power for Electric Vehicles, available online at <file: //usm-filvp01/USM-Data/Paralegals/Client%20Folders/InTouch%20Health%20-%2080525/I . . . >, retrieved on Dec. 1, 2011, 2 pages.

"Nomad Scout Language Reference Manual", Nomadic Technologies, Software Version 2.7, Part No. DOC00002, Jul. 12, 1999, pp. 1-47.

"Opening Brief for Plaintiff-Appellant InTouch Technologies, Inc.", Appeal from the U.S. District Court for the Central District of California in Case No. 11-cv-9185, Judge Percy Anderson, Apr. 12, 2013, 187 pages.

Reply Brief for Defendant-Appellee VGO Communications, Inc., Appeal from the U.S. District Court for the Central District of California, in Case No. 2:11-cv-9185, Judge Percy Anderson, May 28, 2013, 75 pages.

Reply Brief for Plaintiff-Appellant InTouch Technologies, Inc., Appeal from the U.S. District Court for the Central District of California in Case No. 11-cv-9185, Judge Percy Anderson, Jun. 14, 2013, 39 pages.

"MPEG File Format Summary", MPEG: Summary from the Encyclopedia of Graphics File Formats, Available Online at <http://www.fileformat.info/format/mpeg/egff.htm>, retrieved on Jun. 25, 2014, 7 pages.

Using your Infrared Cell Phone Camera, online available at <http://www.catsdomain.com/xray/about.htm>, retrieved on Jan. 23, 2014, 4 pages.

Office Action Received for Chinese Patent Application No. 200680044698.0, dated Nov. 4, 2010, 26 pages. (17 pages of English Translation and 9 pages of Official copy).

"Saphira" Software Manual, ActiveMedia, Inc., Saphira Version 5.3, Mar. 1997, 105 pages.

Pioneer 2/PeopleBotTM, Operations Manual, ActivMedia Robotics, Version 9, Oct. 2001, 78 pages.

"Nomad Scout User's Manual", Nomadic Technologies, Jul. 12, 1999, pp. 1-59.

Apple Inc., I Phone, iPhone Series, XP002696350, Sep. 21, 2012, pp. 1-29.

Bradner, S., "The Internet Standards Process—Revision 3", Oct. 1996, pp. 1-36.

Christensen et al., Robots for the Real World™, Real World Interface, Inc., BeeSoft User's Guide and Reference, Sep. 26, 1997, 203 pages.

"Helpmate, the Trackless Robotic Courier", PYXIS, 2007, 3 pages.

Fulbright et al., "Swami: An Autonomous Mobile Robot for Inspection of Nuclear Waste of Storage Facilities", Autonomous Robots, vol. 2, 1995, 225-235.

Gaidioz et al., "Synchronizing Network Probes to Avoid Measurement Intrusiveness with the Network Weather Service", Proceedings of the Ninth International Symposium on High-Performance Distributed Computing, 2000, pp. 1-8.

Garner et al., "The Application of Telepresence in Medicine", BT Technology Journal, vol. 15, No. 4, Oct. 1, 1997, 4 pages.

Gostai, "Gostai Jazz: Robotic Telepresence", Available online at <http://www.gostai.com>, 4 pages.

Jacobs et al., "Applying Telemedicine to Outpatient Physical Therapy", AMIA, Annual Symposium Proceedings, 2002, 1 page.

Kurlowicz et al., "The Mini Mental State Examination (MMSE)", Try This: Best Practices in Nursing Care to Older Adults, A series from the Hartford Institute of Geriatric Nursing, No. 3, Jan. 1999, 2 pages.

Leifer et al., "VIPRR: A Virtually in Person Rehabilitation Robot", online available at <http://www.stanford.edu/group/rrd/People/vdl/publications/ICORR97/VIPRR.html>, retrieved on Aug. 3, 2012, 4 pages.

Lemaire, Edward, "Using Communication Technology to Enhance Rehabilitation Services: A Solution Oriented User Manual", Institute for Rehabilitation Research and Development, Terry Fox Mobile Clinic, The Rehabilitation Centre, Version 2.0; 1998-2001, 104 pages.

Minsky, Marvin, "Telepresence", OMNI Magazine, online available at <web.media.mit.edu/~minsky/papers/Telepresence.html>, Jun. 1980, 6 pages.

Nakazato et al., "Group-Based Interface for Content-Based Image Retrieval", Proceedings of the Working Conference on Advanced Visual Interfaces, 2002, pp. 187-194.

Nakazato et al., "Group-Oriented User Interface for Digital Image Management", Journal of Visual Languages & Computing, vol. 14, No. 4, Aug. 2003, pp. 45-46.

North, Michael, "Telemedicine: Sample Script and Specifications for a Demonstration of Simple Medical Diagnosis and Treatment Using Live Two-Way Video on a Computer Network", Greenstar Corporation, 1998, 5 pages.

Osborn, Jim, "Quality of Life Technology Center", QoLT Research Overview:A National Science Foundation Engineering Research Center, Carnegie Mellon University of Pittsburgh, 2 pages.

Piquepaille, Roland, "This Blog and its RSS Feed Are Moving", Roland Piquepaille's Technology Trends, How New Technologies are Modifying Our Way of Life, Oct. 31, 2004, 2 pages.

Radvision, "Making Sense of Bandwidth the NetSense Way", Network Congestion in Unmanaged Networks Bandwidth Estimation and Adaptation Techniques,Radvision White Paper, 2010, 7 pages.

Reynolds et al., "Review of Robotic Telemedicine Utilization in Intensive Care Units (ICUs)", 11th Annual ATA Symposium, Tampa, Florida, 2011, 1 page.

Telepresence Research, Inc. "The Telepresence Mobile Robot System", Available online at: http://www.telepresence.com/telepresence-research/TELEROBOT/, Retrieved on Nov. 23, 2010, 3 pages.

Theodosiou et al., "MuLVAT: A Video Annotation Tool Based on XML-Dictionaries and Shot Clustering", ICANN, Part II, LNCS 5769, 2009, pp. 913-922.

Tipsuwan et al., "Gain Adaptation of Networked Mobile Robot to Compensate QoS Deterioration", vol. 4, 28th Annual Conference of the Industrial Electronics Society, Nov. 5-8, 2002, pp. 3146-3151.

Tsui et al., "Exploring Use Cases for Telepresence Robots", 6th ACM/IEEE International Conference on Human-Robot Interaction (HRI), Mar. 6-9, 2011, 8 pages.

Tyrrell et al., "Teleconsultation in Psychology: The Use of Videolinks for Interviewing and Assessing Elderly Patients", Age and Ageing, vol. 30, May 2001, pp. 191-195.

UMASS Lowell Robotics Lab, "Robotics Lab @ UMASS Lowell", Brochure, 2011, 2 pages.

Video Middleware Cookbook, "H.350 Directory Services for Multimedia", available online at <http:/ /lab.ac.uab.edu/vnetl>, 2 pages.

"Autonomous Robots", ACM, Digital Library, vol. 11, No. 1, Jul. 2001, 2 pages.

Blaer et al., "TopBot: Automated Network Topology Detection With a Mobile Robot", IEEE, Proceedings of the 2003 International Conference on Robotics 7 Automation, Taipei, Sep. 14-19, 2003, pp. 1582-1587.

Brenner, Pablo, "A Technical Tutorial on the IEEE 802.11 protocol", BreezeCOM Wireless Communications, 1997, pp. 1-24.

Chu et al., "Detection of Target Mobile Signal Strength", Technical Developments, Motorola Inc., Jan. 1, 1999, 3 pages.

CMU Course "16x62 Robot User's Manual", Describing the Nomad Scout, Carnegie Mellon University, Feb. 1, 2001, 11 pages.

* cited by examiner

FIG. 4

New Patient — 400

- First name — 410: John
- Last name — 412: Smith
- Medical record number — 414: 10101010
- Admission date (local time) — 416: 2010 / December / 30 / 11 : 28
- Date of birth — 418: 04 / January / 1935
- Age — 420: 75
- Gender — 422: Male
- Chief complaint — 424: Chest Pain
- Allergies — 426: Penicillin
- Medications — 428: Aspirin
- Location — 430: InTouch Health
- Create — 432

FIG. 2

Login — 200

- Username — 210
- Password — 212
- Login — 214

FIG. 3

Patient Work List — 300

- Create a New Patient — 310

FIG. 5

Patient Work List

Patient Smith, John was successfully created

Create new patient

| | | Show Patients Created in Past: 30 Days ▼ |
|---|---|---|
| Smith, John  MRN: 10101010 | View/Create Documents  502 | Edit Patient  504 / Delete Patient  506 |
| Location: InTouch Health | Admitted: Dec 30 2010 11:28 PST  ← 508 |
| Date of Birth: 01/04/1935 | Age: 75 |
| Allergies: Penicillin | Medications: Aspirin |
| Chief Complaint: Chest Pain | Gender: Male |

Document – Smith, John

Orders (602) | Notes (604) | Charge Data Capture Forms (606)

608 — Create a New Document

There are no orders assigned to this patient.

Create New Patient Document

Patient:
Smith, John

Document Category: ⟋702

[ ⌄ ]
Progress Note
Charge Capture
Physician Order

[Create] ⟋214

FIG. 7B

Create New Patient Document

Patient:
Smith, John

Document Category: ⟋702
[ Physician Order ⌄ ]

Document Name: ⟋704
[ ⌄ ]
Discharge Order
Laboratory Order
Potassium Replacement Order

[Create] ⟋704

FIG. 8

Potassium Replacement Order for Smith, John

Sign Document 802  Close Document 804  Back to Patient Documents

800

GENERAL HOSPITAL

POTASSIUM REPLACEMENT ORDER

Patient Full Name: John Smith
MRN: 10101010
Date of Birth: 01/04/1935
Date of Admission: 12-30-10 11:28 PST
First Name: John
Last Name: Smith
Gender: ☑ Male ☐ Female ☐ Unknown
Age: 75

Physicians must delete any order that does not apply by drawing a line through the order and initialing.

POTASSIUM REPLACEMENT ORDER
For Treatment of Hypokalemia
(low blood potassium level)

GENERAL COMMENTS:
1. Route of administration (eternal versus paternal) to be determined by RN and/or MD
2. Eternal route of potassium replacement (oral, vial NGT, OGT, or PEG tube) is preferable over intravenous when possible

| ORDERS NOTED | | Nurses signature | Time Noted |
|---|---|---|---|
| | | | |
| | | | |
| | | | |
| | | | |
| | | | |

Options

FIG. 9

Signed Document Notification

Would you like to notify a user that this document has been signed?

Select Recipient: 902

John Doe
Jane Doe
Tom Smith

Send 214

FIG. 10

Patient Worklist

E-Mail notification was sent to Tom Smith

Create new patient 1002

Smith, John  MRN: 10101010

Location: InTouch Health
Date of Birth: 01/04/1935
Allergies: penicillin
Chief Complaint: Chest Pain

SYSTEMS AND METHODS FOR MANAGEMENT OF INFORMATION AMONG MEDICAL PROVIDERS AND FACILITIES

BRIEF DESCRIPTION OF THE DRAWINGS

FIG. 2 illustrates a screen shot of a login screen, according to one embodiment of a system for management of information among medical providers and facilities.

FIG. 3 illustrates a screen shot of a patient work list screen, according to one embodiment of a system for management of information among medical providers and facilities.

FIG. 4 illustrates a screen shot of any new patient screen, according to one embodiment of a system for management of information among medical providers and facilities.

FIG. 5 illustrates a screen shot of a patient work list, according to one embodiment of a system for management of information among medical providers and facilities.

FIG. 6. illustrates a screen shot of a page displaying documents associated with a patient, according to one embodiment of a system for management of information among medical providers and facilities.

FIG. 7A illustrates a screen a shot of a page for creating a new document, according to one embodiment of a system for management of information among medical providers and facilities.

FIG. 7B illustrates a screen a shot of the page for creating a new document illustrated in FIG. 7A.

FIG. 8 illustrates a screen shot of a page including a location-specific physician order form, according to one embodiment of a system for management of information among medical providers and facilities.

FIG. 9 illustrates a screen shot of a signed document notification page, according to one embodiment of a system for management of information among medical providers and facilities.

FIG. 10 illustrates a screen shot of a patient work list that displays confirmation that an e-mail notification was sent, according to one embodiment of a system for management of information among medical providers and facilities.

DETAILED DESCRIPTION OF PREFERRED EMBODIMENTS

Figure 1:
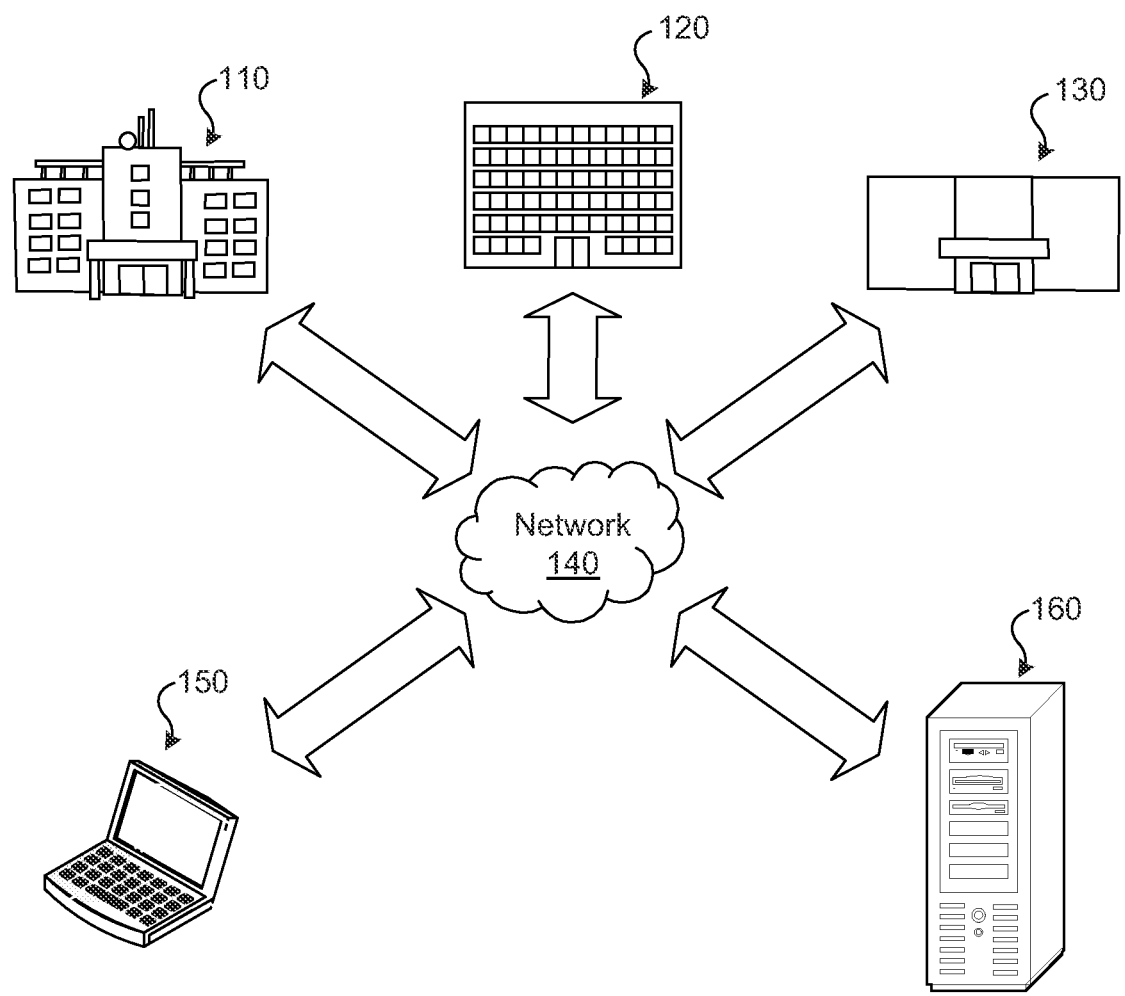
FIG. 1 illustrates a conceptual diagram of one environment in which systems and methods for management of information among medical providers and facilities may be utilized.

Many medical providers and facilities rely heavily on the tracking of patient information in order to improve patient care and consistency. Frequently, medical providers and/or facilities generate forms that are to be used by medical professionals in order to track patients, record diagnoses, provide medical orders, etc. In order to improve consistency, many medical providers and/or facilities mandate the use of particular forms. Further, the procedures for carrying out the implementation of medical orders may also vary among facilities. Considerable effort may be needed for a medical professional to become familiar with each of the mandatory forms and procedures established by a medical facility.

Similar information may be recorded by various medical facilities in similar situations; however, a lack of familiarity with a particular organization's forms and procedures may decrease the effectiveness of a medical professional. For example, where a patient presents at a medical facility complaining of stroke-related symptoms, certain information may be universally sought (e.g., the patient's name, age, weight, medical history, etc.). Some institutions may track other types of data that are not universally sought, such as the patient's NIHSS at arrival, the patient's NIHSS at discharge, the patient's eligibility for t-PA, etc.). Depending on the particular institution, these data and a variety of other types of information may be included on a form; however, the organization of information on the form may be unique to a particular facility.

Medical professionals using telemedicine technologies may practice in more than one medical facility. Use of different forms and procedures at different medical facilities may increase the administrative burden on medical professionals utilizing telemedicine technologies, since the practitioner may need to become familiar with each facility's unique forms and procedures. Further, the variation in the forms and procedures among various medical facilities may undermine the effectiveness of a medical professional providing services in a variety of medical facilities.

As a further complication for medical professionals utilizing telemedicine technologies, forms utilized by some medical providers and/or facilities may only be available in paper. Maintaining a patient file utilizing paper forms may be challenging for a remotely located medical professional. For example, it may be impractical for a remotely located medical professional utilizing telemedicine technologies to have paper forms available for every procedure for every medical facility in which the medical professional may provide services. Similarly, in medical facilities utilizing digital forms or databases, considerable variation in electronic systems may make it impractical for a medical professional utilizing telemedicine technologies to become intimately familiar with the electronic systems of each medical facility.

Disclosed herein are various embodiments of the systems and methods for management of information among various medical providers and/or facilities. According to various embodiments, the systems and methods disclosed herein may facilitate the completion of forms in a variety of formats by medical professionals utilizing telemedicine technologies. Such systems may provide medical professionals utilizing telemedicine technologies with a consistent interface for gathering and inputting patient information, while continuing to allow for the use of a wide variety of forms by different medical providers and facilities. For example, a system according to the present disclosure may store patient information and/or medical orders received from a medical professional in a database. Information from the database may then be used to populate a location-specific form used by the medical facility in which a particular patient is being treated. Once the patient information has been gathered and the form has been populated, the system may undertake actions consistent with procedures established by the particular medical facility.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. In particular, an "embodiment" may be a system, an article of manufacture (such as a computer-readable storage medium), a method, and a product of a process.

The phrases "connected to," and "in communication with" refer to any form of interaction between two or more entities, including mechanical, electrical, magnetic, and electromagnetic interaction. Two components may be connected to each other even though they are not in direct contact with each other and even though there may be intermediary devices between the two components.

The embodiments of the disclosure will be best understood by reference to the drawings, wherein like elements are designated by like numerals throughout. In the following description, numerous specific details are provided for a thorough understanding of the embodiments described herein. However, those of skill in the art will recognize that one or more of the specific details may be omitted, or other methods, components, or materials may be used. In some cases, operations are not shown or described in detail.

Furthermore, the described features, operations, or characteristics may be combined in any suitable manner in one or more embodiments. The order of the steps or actions of the methods described in connection with the embodiments disclosed may be varied. Thus, any order in the drawings or Detailed Description is for illustrative purposes only and is not meant to imply a required order, unless specified to require an order.

Embodiments may include various features, which may be embodied in machine-executable instructions executed by a general-purpose or special-purpose computer (or other electronic device). Alternatively, the features may be performed by hardware components that include specific logic for performing the steps or by a combination of hardware, software, and/or firmware.

Embodiments may also be provided as a computer program product including a non-transitory machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

FIG. 1 illustrates a conceptual diagram of one environment in which the systems and methods disclosed herein may be utilized for management of information among a variety of medical providers and facilities. According to the illustrated embodiment, medical facilities 110, 120, and 130 are each connected to network 140. Medical facilities 110, 120, and 130 may be geographically dispersed, and each facility may operate autonomously from each other facility. Medical facilities 110, 120, and 130 may comprise various types of medical facilities (e.g., hospitals, rehabilitation facilities, long-term care facilities, etc.).

Network 140 may facilitate the exchange of information in a variety of formats. For example, network 140 may allow for the exchange of digital data, voice data, the transmission of facsimiles, etc. Network 140 may, according to some embodiments, include separate networks (e.g., a data network and a voice network). Network 140 may comprise a variety of networking technologies and components and may facilitate the exchange of data in secure forms of communication. For example, network 140 may represent the Internet, and communications between a remote terminal 150, a server 160, and medical facilities 110, 120, and 130, may be encrypted during transmission via network 140. Network 140 may further comprise a virtual private network ("VPN") established for the exchange of data. According to other embodiments, network 140 may be a private network.

Medical facilities 110, 120, and 130 may include telemedicine technologies that may be accessed by a remote medical professional using terminal 150 and network 140. A variety of types of telemedicine technologies may be utilized in connection with the systems and methods disclosed herein. The remote medical professional using terminal 150 may provide specialty services that may not otherwise be locally available in medical facilities 110, 120, and 130. For example, the remote medical professional may be a neurologist and medical facilities 110, 120, and 130 may be hospitals located in rural areas that may otherwise not have a neurologist on staff. The neurologist may be available for consultation when a patient presents in any of medical facilities 110, 120, and 130 with a neurological condition (e.g., a stroke, a head injury, a spinal cord injury, etc.).

Medical facilities 110, 120, and 130 may mandate the use of different forms and procedures. Accordingly, in the illustrated embodiment, the remote medical professional using terminal 150 may be required to manage the information requirements and procedures of each of medical facilities 110, 120, and 130. Server 160 may provide a variety of systems and methods for facilitating the management of information and procedures relating to each of medical facilities 110, 120, and 130.

Server 160 may comprise a database accessible to the remote medical professional that includes location-specific forms mandated by each of medical facilities 110, 120, and 130. Server 160 may also comprise a database of patient information that includes some or all of the information to be provided on the various forms mandated by each of medical facilities 110, 120, and 130. Server 160 may populate data fields in the location-specific forms using information from the database. Accordingly, the remote medical professional using terminal 150 may utilize a single interface (e.g., a database interface) for providing information using a variety of location-specific forms mandated by each of medical facilities 110, 120, and 130.

The database of patient information may include a patient location (e.g., an indication of whether a patient is located in medical facility 110, medical facility 120, or medical facility 130. Based on a patient's location, the appropriate location-specific form may be automatically selected and populated using data from the patient information database. A variety of other types of data may also be gathered and included within the database of patient information. According to certain embodiments, the types of patient information to be collected and stored within the database may be customizable by an end user. Further, in certain embodiments a user may customize the user interface in order to suit the user's individual preferences.

FIGS. 2-10 illustrate screen shots of an illustrative system for management of information among medical providers and facilities. According to various embodiments, users may interact with systems according to the present disclosure in various ways, such as a server-client architecture or a web-based architecture. The screen shots illustrated in FIG. 2-10 may be adapted for either a client-server architecture or a web-based architecture.

FIG. 2 illustrates a screen shot of a login screen 200. An authorized user may enter a user name in data field 210 and a password in data field 212. The user may then press the login button 214. According to various embodiments, role-based logins may be utilized. For example, roles may be defined as: physician, nurse, staff, administrator. Physicians and nurses may be associated with one or more locations (e.g., one or more medical facilities at which the physician or nurse performs services). Users designated as administrators may be allowed to add locations, delete locations, and associate users with particular locations.

FIG. 3 illustrates a screen shot of a patient work list screen 300. In the illustrated example, the work list does not include any patients. An option for creating a new patient 310 is displayed. If a particular user's work list include patients from previous sessions, a list of such patients may be displayed. In certain embodiments, physicians and nurses logging into the system may be directed to the patient work list by default. Patient work list screen 300 may include a list of all patients at each of a variety of medical facilities associated with the user.

FIG. 4 illustrates a screen shot of a new patient screen 400. New patient screen 400 includes a plurality of data fields 410-430 that may be utilized for recording patient data. According to the illustrated embodiment, the data fields 410-430 may include: a first name field 410, a last name field 412, a medical record number field 414, and an admission date and time field 416, a date of birth field 418, an age field 420, a gender field 422, a chief complaint field 424, an allergies field 426, a medications field 428, and a location field 430. Once the patient information has been entered into the respective data fields 410-430, a user may press the create button 432. Certain of the data fields 410-430 may be mandatory, and a user may not proceed with the creation of a new patient until all mandatory data fields are completed. According to one embodiment, mandatory data fields may include the patient's name, location, an admission date. Certain of the data fields may include a default value. For example the admission date may include the current date and time by default. The use of default values may increase the speed with which patient data may be entered.

FIG. 5 illustrates a screen shot of a patient work list 500 that includes an examplary patient, John Smith. Patient work list 500 includes demographic information about the patient. Various options are provided, including options to "View/Create Documents" 502, "Edit Patient" 504, and "Delete Patient" 506. Clicking on the link to "Edit Patient" 504 may display the patient's demographic information in editable fields so that the information can be updated. Clicking on the link to "View/Create Documents" 502 may direct a user to a page displaying all documents associated with the patient. According to various embodiments, each user may be allowed to customize the display of data appearing on the user's patient work list 500. For example, one physician may desire to have a detailed view of each patient on the patient work list 500, and accordingly, may customize the patient work list 500 to display additional information. In contrast, another physician may desire to limit the amount of data displayed for each individual patient.

FIG. 6. Illustrates a screen shot of a page 600 displaying documents associated with a patient. Categories of documents may be grouped together. According to the illustrated embodiment, categories include orders 602, notes 604, and charge data capture forms 606. A user may view documents in each category by selecting the tab of a desired category of documents. Further, a user may create a new document by selecting the link "Create a New Document" 608. According to certain embodiments, unsigned documents may only be visible to the creator of the document, while signed documents may be visible to other users. Further, options may be presented for sending signed documents via e-mail or facsimile to a specified recipient. Options for sending documents may be restricted based on a user's role or other criteria.

The categories of documents illustrated in FIG. 6 are merely illustrative of various organizational arrangements that may be utilized in various embodiments. According to the illustrated embodiment, orders 602 may include physician orders for care relating to a particular patient (e.g., treatment regimens, laboratory tests, etc.). Notes 604 may relate to periodic evaluations regarding the patient's status. Finally, charge data capture forms 606 may relate to chargeable services. Location-specific billing documents may be created, edited, and signed, via the same system used for creating documents relating to patient care. Embodiments allowing for the creation of billing documents may reduce the number of systems that a medical professional must learn, and may thus improve the efficiency of the medical professional when operating in multiple medical facilities.

FIGS. 7A and 7B illustrate screen shots of a page for creating a new patient document 700. A user may specify a document category 702 and a document name 704. After selecting a document category 702, the list of documents shown in the document name data field 704 may be limited to documents within the selected category. Further, the document name data field 704 may be limited to the location-specific forms available for the facility where the selected patient is receiving care. According to the illustrated example, a user has selected "physician order" as the document category and "potassium replacement order" as the document name. After selecting a desired document category and document name, a user may press the create button 704.

FIG. 8 illustrates a screen shot 800 of a page including a location-specific physician order form for potassium replacement. As described above, the location at which a patient is being treated is entered into the system when the patient's record is created. Accordingly, when a particular form for the patient is created (e.g., the potassium replacement order form) the system may automatically select the appropriate location-specific form. Further, additional patient information previously entered into the system may be used to populate various data fields in the location-specific form. In the illustrated example, the patient's name, medical record number, date of birth, date of admission, gender, and age may all be automatically placed in the appropriate areas of the location-specific form. According to various embodiments, data fields that are not populated using previously provided patient information may be entered by a user in screen 800. According to other embodiments, upon the selection of a location-specific form, a page may be displayed in which each data field is presented. The user may provide the appropriate information, which may then be incorporated into the location-specific form. A user may close a document using the "close document" link 804. A user may also electronically sign a document using the "sign document" link 802. After signing a document, a user may be prompted to provide notification of the signed document.

FIG. 9 illustrates a screen shot of a signed document notification page 900. A user may select a recipient using data field 902. Various forms of notification may be available, including e-mail and facsimile. Recipients listed in data field 902 may have a default method of communication, and notification of a signed document may be transmitted according to the recipient's default method of communication. Where e-mail is used as the default method of communication, the e-mail may include text notifying the recipient that a document has been signed. The e-mail message may include a link directing a recipient to a login page. Upon successful authentication, the recipient may view the signed document. According to some embodiments, patient health information is not transmitted via e-mail. Where facsimile is used as the default method of communication, the signed document may be transmitted directly to the specified recipient.

FIG. 10 illustrates a screen shot of a patient work list 1000 that displays confirmation 1002 that an "E-mail notification was sent to Tom Smith."

In addition to facilitating the use of location-specific forms, the systems and methods for management of information disclosed herein may also be used for the collection of patient care metrics. Analysis of patient care metrics may allow for improvement of procedures within a medical facility. For example, a medical facility may desire to assess the performance stroke diagnosis utilizing telemedicine technologies. A system according to the present disclosure may be developed in order to track data associated with stroke diagnosis. In one example, a facility may include the following data fields in a location-specific form to be used whenever a stroke is diagnosed:

Time elapsed: Onset to Arrival
Time elapsed: Arrival to t-PA delivered
Time elapsed: Arrival to imaging available
Time elapsed: Arrival to imaging reviewed
Binary: Eligible for t-PA
Binary: Received t-PA
Binary: Patient history indicators (stroke/tia, diabetes, hypertension, etc . . . )
Value: NIHSS at arrival
Value: NIHSS at discharge
Binary: Transferred Other criteria and/or metrics may be specified and developed for tracking patient care associated with other diagnoses (e.g., heart-attacks, trauma, etc.). Patient care metrics may be compiled and available as needed for analysis.

Figure 11:
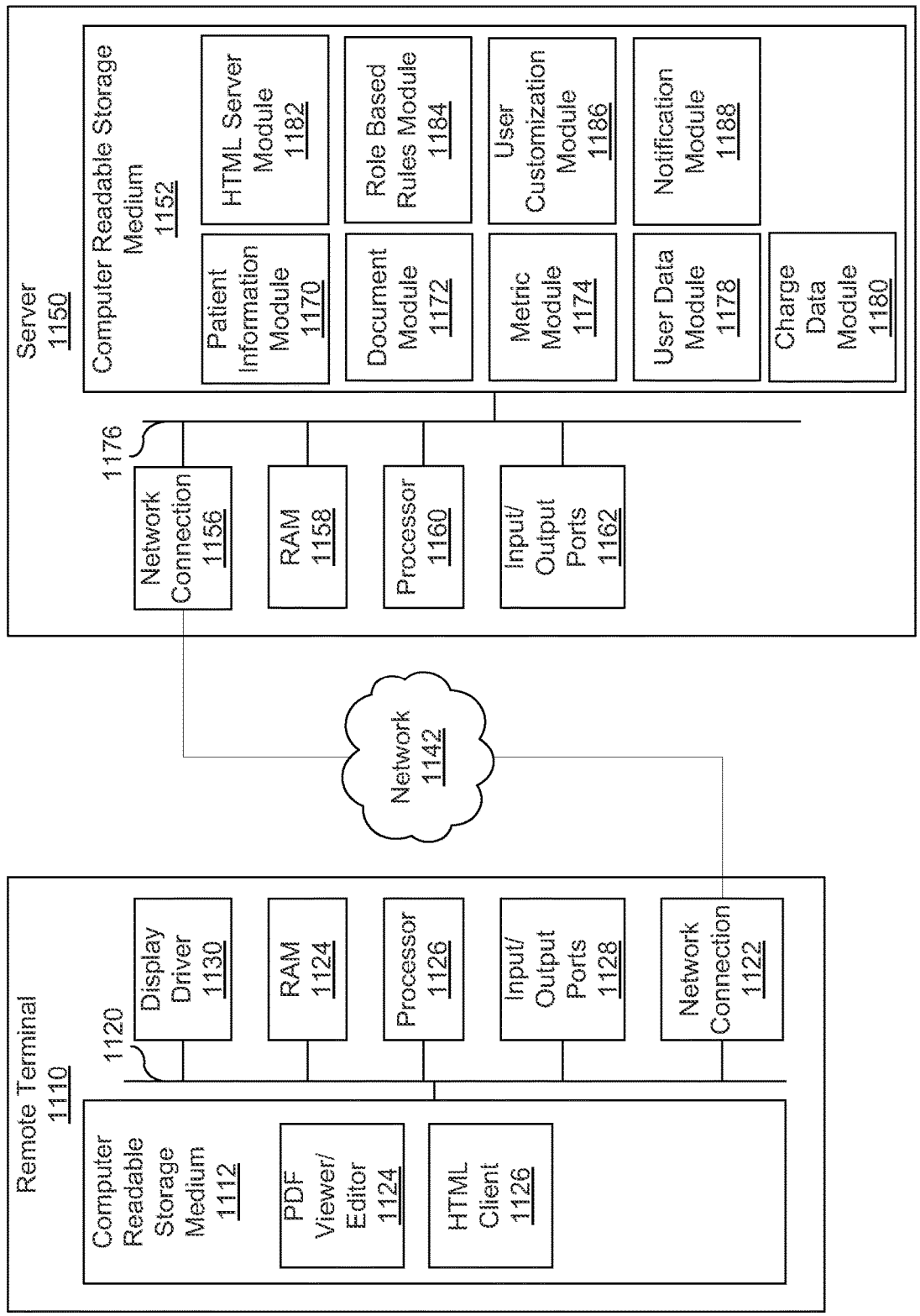
FIG. 11 illustrates a functional block diagram of one embodiment of a system for management of information among various medical providers and facilities.

FIG. 11 illustrates a functional block diagram of one embodiment of a system 1100 for management of information among various medical providers and facilities. System 1100 includes a remote terminal 1110, a network 1142, and a server 1150. System 1100 allows remote terminal 1110 to exchange data with server 1150 via network 1142. Although not shown in FIG. 11, various medical facilities may also interface with system 1100, in a configuration that may be similar to the embodiment illustrated in FIG. 1.

Remote terminal 1110 includes a network connection 1122, Random Access Memory (RAM) 1124, processor 1126, input/output ports 1128, a display driver 1130, a computer-readable storage medium 1112, and a bus 1120. Bus 1120 provides a connection between network connection 1122, input/output ports 1128, RAM 1124, display driver 1130, processor 1126, and computer-readable storage medium 1112. Processor 1126 may be embodied as a general purpose processor, an application specific processor, a microcontroller, a digital signal processor, or other similar device. Processor 1126 performs logical and arithmetic operations based on executable program code stored within RAM 1124 and/or computer-readable storage medium 1112.

Network connection 1122 may be configured to communicate with network 1142 by way of one or more network components (e.g., firewalls, routers, etc.). Network connection 1122 may facilitate communication using any number of available protocols and/or physical media. Network 1142 may comprise an intranet, a virtual private network, or a public network, such as the Internet or other data communications networks. According to various embodiments, network management techniques may be utilized to successfully route data from remote terminal 1110 to server 1150.

Input/output ports 1128 may be configured to allow remote terminal 1110 to utilize a variety of peripheral devices, some of which may generate data to be transmitted to server 1150. For example, peripheral devices which may be utilized may include a video camera, a microphone, a keyboard, a mouse, and other such devices. Input/output ports 1128 may comprise a variety of types of ports, such as USB, serial, parallel, IEEE 1394, and the like.

Display driver 1130 may facilitate the generation of video images to be displayed to a user remote terminal 1110. For example, display driver 1130 may display for a user a variety of forms generated by server 1150 and transmitted via network 1142.

Computer-readable storage medium 1112 may comprise various modules for communicating with server 1150. Such modules may include an HTML client 1126 and a PDF viewer/editor 1124. HTML client 1126 may be configured to receive data according to the hypertext markup language, or other suitable format for communicating data via network 1142, (e.g., XML). PDF viewer/editor 1124 may be configured to display and/or edit a document in the Portable Document Format ("PDF"). In alternative embodiments, more or fewer modules than are shown in FIG. 11 may be utilized.

According to various embodiments, remote terminal 1110 may be embodied as a general purpose computer including particular software and/or configured to interface with server 1150. Such software may be delivered as a computer program product embodied as a non-transitory computer-readable storage medium.

According to the illustrated embodiment, server 1150 includes a network connection 1156, RAM 1158, a processor 1160, input/output ports 1162, a computer-readable storage medium 1152, and a bus 1176. The function of network connection 1156, RAM 1158, processor 1160, and input/output ports 1162 may be similar to the functions described in connection with corresponding structures in remote terminal 1110.

Computer-readable storage medium 1152 may comprise various modules for communicating with remote terminal 1110 and for managing information among medical providers and facilities. Such modules may include a patient information module 1170, a document module 1172, a metric module 1174, a user data module 1178, a notification module 1188, a charge data module 1180, an HTML server module 1182, a role based rules module 1184, and a user customization module 1186.

Patient information module 1170 may be a repository of information collected regarding a patient. Such information may include demographic information, medical history information, a list of symptoms, a list of medications taken by the patient, etc. Information stored in patient information module 1170 may be made accessible to other modules, such as document module 1172.

Document module 1172 may be a repository of a variety of location-specific forms provided by different medical providers and/or facilities. Upon selection of an appropriate location-specific form, document module 1172 may further retrieve data from patient information module 1170 and populate appropriate data fields in the location-specific form.

Metric module 1174 may be configured to collect various data related to specified metrics. For example, one or more forms may be designated as containing information relevant to a metric. When such information is entered into a form, metric module 1174 may collect such data for later analysis.

User data module 1178 may be configured to be a repository of information regarding various users authorized to access data stored on server 1150. User data module 1178 may further include information regarding the specific roles of each user (e.g., physician, nurse, administrator, etc.). User data module 1178 may further track the various medical facilities at which each user provides services.

Notification module 1188 may be configured to provide notification to one or more designated recipients upon the occurrence of the specified condition. As described above, when a document is signed, notification of the signed document or a copy of the signed document may be delivered to a specified recipient. Notification module 1188 may further comprise default communication preferences for recipients and relevant contact information for such recipients (e.g., e-mail address, a facsimile number, etc.).

Charge data module 1180 may be configured to store information relevant to chargeable services provided by medical professionals utilizing system 1100. Charge data module 1180 may, according to various embodiments, interact with notification module 1188 in order to generate notification of a chargeable event or service.

HTML server module 1182 may be configured to generate HTML-based pages which may be transmitted to remote terminal 1110 and, using which a medical professional may enter data. According to alternative embodiments, HTML server module 1182 may be replaced by another module configured to generate any suitable data format for collecting information from remote terminal 1110.

Role based rules module 1184 may be configured to enforce a plurality of rules based on a user's role. For example, a role based rule may be established allowing users designated in the role of "physician" to sign certain forms. Similarly, a role based rule may be established allowing users designated in the role of "administrators" to associate users with a particular location.

User customization module 1186 may be configured to allow a user to customize the appearance of one or more aspects of a user interface. For example, as described above, a user may customize a patient work list to display a greater amount of patient information or a lesser amount of patient information. Similarly, a variety of other elements of a user interface may be customized to suit a particular user's preferences.

Many changes may be made to the details of the above-described embodiments without departing from the underlying principles of the present disclosure. The scope of the present invention should, therefore, be determined only by the following claims.

The invention claimed is:

1. A method performed by a telemedicine system for generating, by a remote medical professional using a single interface, a plurality of forms complying with different respective requirements of one of a plurality of geographically dispersed medical facilities at which the remote medical professional is authorized to practice without knowledge by the remote medical professional of said different requirements, wherein the telemedicine system comprises at least one processor and at least one non-transitory computer-readable storage medium communicatively coupled to the at least one processor, the at least one non-transitory computer-readable storage medium storing instructions that, when executed by the at least one processor, cause the at least one processor to perform the method, the method comprising:

storing a plurality of location-specific forms in a form database on a server that is coupled to a network, each location-specific form complying with requirements of a different one of the plurality of geographically dispersed medical facilities, the plurality of location-specific forms being organized into categories, wherein storing includes storing at least first and second location-specific forms, wherein a first location-specific form is associated with a first form category and a first medical facility, and wherein a second location-specific form is associated with said first form category and a second medical facility, and wherein said first and second location-specific forms are different;

determining a location for each of a plurality of patients, the location including an identification of one of the plurality of geographically dispersed medical facilities at which each patient is located;

storing, in patient database, patient information on the plurality of patients, the patient information including identifying information for each patient and the location of each patient;

transmitting a patient work list for display at a remote station coupled to the network, the patient work list including information identifying the plurality of patients;

receiving, from the remote station, a selection by the remote medical professional of one of the plurality of patients identified in the patient work list;

receiving, from the remote station, a request by the remote medical professional to generate a form associated with the selected patient, the request including an identification of a form category, and automatically identifying, by the patient database, a medical facility based on the location of the patient;

automatically selecting, by the server, a location-specific form from the form database in response to the request based on the identified medical facility, wherein the server selects said first location-specific form when the requested form category is said first form category and the patient location corresponds to said first medical facility and the server selects said second location-specific form when the requested form category is said first category and the patient location corresponds to said second medical facility;

automatically populating, by the server, at least a subset of the selected location-specific form using the patient information stored in the patient database;

transmitting the selected location-specific form to the remote station for display to the remote medical professional on a display device of the remote station;

prompting the remote medical professional to supply any information in the selected location-specific form not populated using the patient information; and in response to the medical professional electronically signing the selected location-specific form, transmitting the selected location-specific form to the identified medical facility at which the patient is located.

2. The method of claim 1, further comprising: selecting a default method of transmission for the electronically signed location-specific form based on the patient location.

3. The method of claim 2, further comprising: transmitting the electronically signed location-specific form via facsimile.

4. The method of claim 2, further comprising: collecting a subset of the patient information related to a metric.

5. The method of claim 1, further comprising: controlling access to at least one user action based on a role of a user.

6. The method of claim 1, further comprising: customizing at least one aspect of a patient work list based on input received from a user.

7. The method of claim 1, further comprising: generating a location-specific form associated with a chargeable event based on the patient location.

8. The method of claim 6, wherein customizing at least one aspect of the work list comprises selectively adding or removing information displayed for a patient in the patient work list.

9. The method of claim 1, wherein transmitting the patient work list comprises:
- determining one or more medical facilities at which the remote medical professional is authorized to practice; and
- transmitting the patient work list including each patient of the remote medical professional associated with the determined one or more medical facilities.

10. The method of claim 1, wherein the patient work list includes a list of all patients at each of a plurality of medical facilities associated with the remote medical professional.

11. The method of claim 1, wherein the remote medical professional is associated with a role, and wherein transmitting the selected location-specific form to the identified medical facility comprises restricting one or more transmission options based on the role of the remote medical professional.

\* \* \* \* \*